(12) United States Patent
Marchitto et al.

(10) Patent No.: US 6,419,642 B1
(45) Date of Patent: *Jul. 16, 2002

(54) IRRADIATION ENHANCED PERMEATION AND DELIVERY

(75) Inventors: Kevin S. Marchitto, Villa Park, IL (US); Stephen T. Flock, Edmonton (CA)

(73) Assignee: Transmedica International, Inc., Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/589,865

(22) Filed: Jun. 8, 2000

Related U.S. Application Data

(63) Continuation of application No. 08/443,782, filed on Nov. 19, 1999, which is a continuation of application No. 08/955,982, filed on Oct. 22, 1997, now Pat. No. 6,056,738, which is a continuation-in-part of application No. 08/792,335, filed on Jan. 31, 1997, now abandoned, which is a continuation-in-part of application No. 08/126,241, filed on Sep. 24, 1993, now Pat. No. 5,643,252.

(51) Int. Cl.[7] .............................. A61B 5/00; A61N 1/30
(52) U.S. Cl. ............................ 600/573; 606/9; 606/17; 607/89; 604/20; 128/898
(58) Field of Search .............................. 606/9–17, 2–3; 600/573; 128/897–898; 604/20; 607/89, 88

(56) References Cited

U.S. PATENT DOCUMENTS

| | | | | |
|---|---|---|---|---|
| 5,165,418 A | * | 11/1992 | Tankkovich | 606/9 |
| 5,423,803 A | * | 6/1995 | Tankovich | 606/9 |
| 5,713,845 A | * | 2/1998 | Tankovich | 606/9 |

* cited by examiner

*Primary Examiner*—Kevin Shaver
*Assistant Examiner*—Michael Astorino
(74) *Attorney, Agent, or Firm*—Irell & Manella, LLP

(57) ABSTRACT

The present invention provides a method of delivering substances for permeation through the skin of a subject, by energizing the stratum corneum in conjunction with various delivery means including gels and patches. Permeability enhancement or reduced electrical impedance of the skin, increases the variety of substances capable of permeation, and increases the permeation rate and the effectiveness of the permeation, including permeation enhanced by iontophoresis. The method allows for the use of improved delivery means that were previously unavailable.

17 Claims, 27 Drawing Sheets

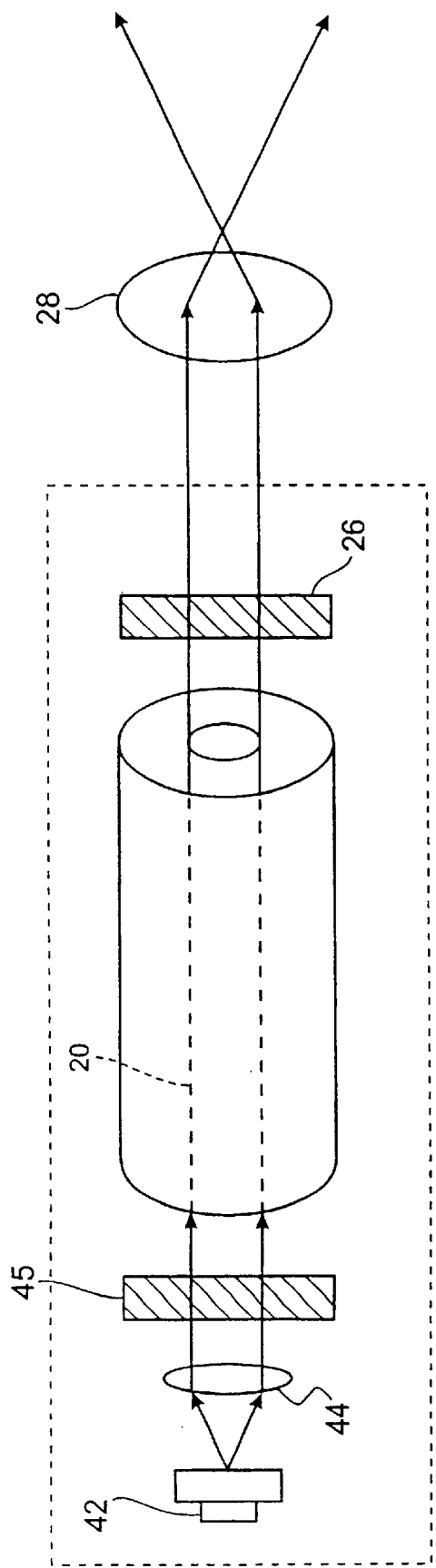
FIG. 3
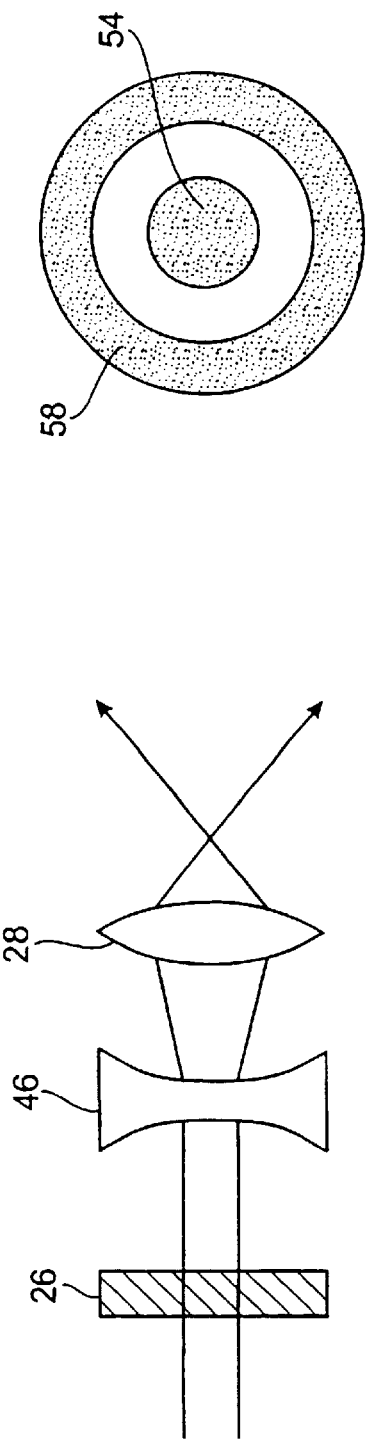
FIG. 6
FIG. 4

▨ TOTAL PERMEATION AFTER 1 HOUR
◨ TOTAL PERMEATION AFTER 3.5 HOURS

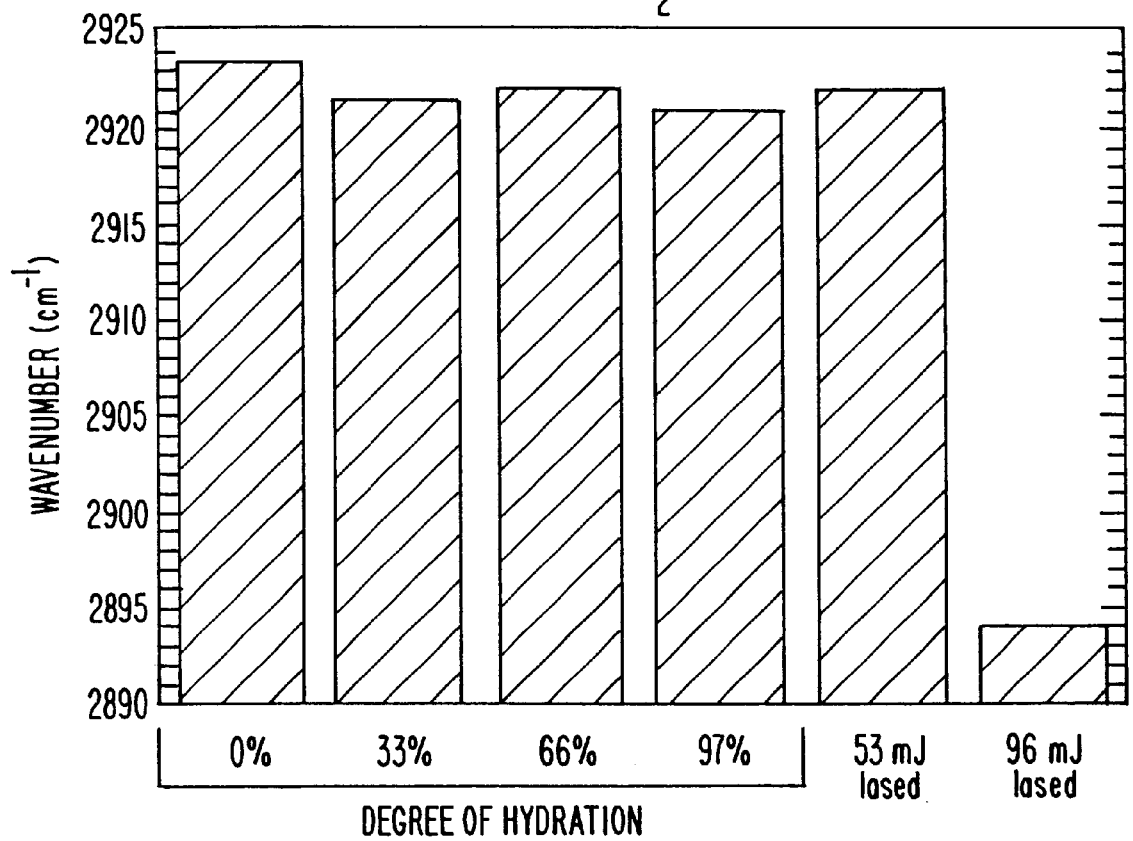

50 mJ Er:YAG LASER IRRADIATION HUMAN SKIN 80 mJ Er:YAG LASER IRRADIATION HUMAN SKIN

IRRADIATION ENHANCED PERMEATION AND DELIVERY

This application is a continuation of pending U.S. application Ser. No. 08/443,782 filed Nov. 19, 1999, which is a continuation of U.S. Ser. No. 08/955,982 tiled Oct. 22, 1997 (now issued as U.S. Pat. No. 6,056,738), which is a continuation-in-part of U.S. Ser. No. 08/792,335 filed Jan. 31, 1997 (now abandoned), which in turn is a continuation-in-part of U.S. Ser. No. 08/126,241 filed Sep. 24, 1993 (now issued as U.S. Pat. No. 5,643,252), all of which applications are incorporated herein by reference.

FIELD OF THE INVENTION

This invention is in the field of medical procedures, namely, procedures facilitated primarily by laser medical equipment used in the delivery of pharmaceuticals or the removal of biomolecules, fluids or gases.

BACKGROUND

The traditional method for the collection of small quantities of fluids or gases from a patient utilizes mechanical perforation of the skin with a sharp device such as a metal lancet or needle. Additionally, the typical method of administering local anesthetic is through the use of a needle. These procedures have many drawbacks, two of which are the possible infection of health-care workers or the public at large with the device used to perforate the skin, and the costly handling and disposal of biologically hazardous waste.

When skin is perforated with a sharp device such as a metal lancet or needle, biological waste is created in the form of the "sharp" which is contaminated by the patient's blood and/or tissue. If the patient is infected with any number of blood-born agents, such as human immunodeficiency virus(HIV) which causes acquired immune deficiency syndrome (AIDS), hepatitis virus or the etiological agent of other diseases, the contaminated sharp can pose a serious threat to others who come in contact with it. There are many documented instances of F11V infection of medical workers who were accidentally stabbed by a contaminated sharp.

Disposal of sharps is also a major problem. Disposal of contaminated materials poses both a logistic and a financial burden on the end user such as the medical institution. In the 1980s, numerous instances of improperly disposed biological wastes being washed up on public beaches occurred. The potential for others, such as intravenous drug users, to obtain improperly disposed needles is also problematic.

There exist additional drawbacks to the traditional method of stabbing a patient with a sharp instrument for the purpose delivering pharmaceutical agents or for drawing fluids or gases. Often, the stabbing procedure must be repeated, often resulting in significant stress and anxiety in the patient. The pain associated with being stabbed by a sharp instrument can be a traumatizing procedure, especially in pediatric patients. This can cause significant stress and anxiety in the patient.

Clearly the current procedure for puncturing skin for the purpose of drawing fluids or gases has significant inherent problems. These problems arise because a sharp instrument is used in the procedure. Thus, a need exists for techniques to remove biomolecules, fluids or gases, and to administer pharmaceutical agents, which do not use a sharp instrument. Such methods would obviate the need for disposal of contaminated instruments, and reduce the risk of cross infection.

The current technology for applying pharmaceutical substances without the use of needles typically involves: (a) drug mixtures in creams, lotions or gels; (b) iontophoresis, (c) carriers or vehicles which are compounds that alter the chemical properties of either the stratum corneum or the pharmaceutical; (d) sonophoresis which involves altering the barrier function of stratum corneum by ultrasound; or (e) drug patches which attach to the skin to effect transdermal administration. For example, lidocaine is commonly used as a local anesthetic, especially in pediatric patients, but requires a cream to be applied for up to 60 minutes, and anesthesia is produced to a depth of only about 4 mm. The lack of penetration is a consequence of the barrier function of the stratum corneum. Inherent problems with iontophoresis include the complexity of the delivery system, cost, and unknown toxicology of prolonged exposure to electrical current. Additionally, the use of carriers or vehicles involves the use of an additional compound which might alter the pharmacokinetics of the pharmaceutical of interest. Finally, most patch applications are insufficient because many drugs do not easily traverse the stratum corneum.

Clearly a need exists for a means to apply pharmaceutical substances without the use of a needle. The current procedure for applying pharmaceuticals without the use of a needle puncture has inherent problems. The discoveries disclosed herein reduce or eliminate the problems associated with disposal of contaminated needles or sharps, reduce or eliminate the pain associated with being stabbed by a sharp instrument, and improve transdermal delivery of drugs.

Lasers have been used in recent years as a very efficient and precise tool in a variety of surgical procedures. Among potentially new sources of laser radiation, the rare-earth elements are of major interest for medicine. The most promising of these is a YAG (yttrium, aluminum, garnet) crystal doped with erbium (Er) ions. With the use of this crystal, it is possible to build an Erbium:YAG (Er:YAG) laser which can be configured to emit electromagnetic energy at a wavelength (2.94 microns) which is strongly absorbed by water. When tissue, which consists mostly of water, is irradiated with radiation at or near this wavelength, it is rapidly heated. If the intensity of the radiation is sufficient, the heating is rapid enough to cause the vaporization of tissue. Some medical uses of Er:YAG lasers have-been described in the health-care disciplines of dentistry, gynecology and ophthalmology. See, e.g., Bogdasarov, B. V., et al., "The Effect of YAG:Er Laser Radiation on Solid and Soft Tissues," Preprint 266, Institute of General Physics, Moscow, 1987; Bol'shakov, E. N. et al., "Experimental Grounds for YAG:Er Laser Application to Dentistry," SPIE 1353:160–169, Lasers and Medicine (1989).

Er:YAG lasers, along with other solid state lasers often employ a polished barrel crystal element such as a polished rod. A laser built with such a polished element maximizes the laser's energy output. Other lasers employ an entirely frosted element, normally with matte of about 50–55 micro inch. However, in both cases, the energy output is typically separated into a central output beam surrounded by halo rays, or has an otherwise undesirable mode. Since it is extremely difficult to focus halo rays to a specific spot, the laser output may be unacceptable for specific applications.

Solid state lasers also typically employ two optic elements in connection with the crystal element. The optic elements consist of the rear (high reflectance) mirror and the front partial reflectance mirror, also know as an output coupler. The crystal element and the optic elements are rigidly mounted in order to preserve the alignment between them.

However, changes in temperature, such as that caused by expansion of the crystal rod during flash lamp exposure, also cause shifts in alignment between the mirrors and the crystal. The misalignment of the mirrors and the crystal element results in laser output energy loss. Thus, the rigidly mounted elements require constant adjustment and maintenance. Moreover, thermal expansion of the crystal element during lasing can cause the crystal to break while it is rigidly attached to a surface with different expansion characteristics.

SUMMARY OF THE INVENTION

The present invention primarily employs a laser to perforate, ablate or alter one or more layers of the skin of a patient in order to remove biomolecules, fluids or gases, or to administer pharmaceutical substances. Alteration of a patient's skin is produced by irradiating the surface of the skin by a pulse of electro magnetic energy emitted by a laser. Such irradiation may merely enhance the permeability of the stratum corneum without causing ablation (vaporization) or perforation of tissue; alternatively, it may enhance the skin's permeability by ablating or perforating the stratum corneum, or it may enhance the permeation of molecules by altering such intercellular or intracellular molecules. It is possible to very precisely alter skin or permeability to a selectable extent without causing clinically relevant damage to healthy proximal tissue; the depth and extent of alteration may be accomplished by a judicious selection of the following irradiation parameters: wavelength, energy fluence (determined by dividing the energy of the pulse by the area irradiated), pulse temporal width and irradiation spot size.

A pulsed laser beam may be focused to a small spot for the purpose of perforating or altering tissue. By adjusting the output of the laser, the depth, width and length of the perforation or alteration can be controlled to fit the purpose for which the perforation or alteration is required. Alternatively continuous-wave or diode lasers may be used to duplicate the effect of a pulsed laser beam. These modulated lasers are controlled by Q-switching or gating the output of a continuous wave laser or fluctuating the output excitation current in a diode laser. In either case the overall effect is to achieve brief irradiation, or a series of brief irradiations, that produce the same controlled tissue permeabilizing effect as a pulsed laser.

This invention provides a means for perforating or altering the skin of a patient in a manner that does not result in bleeding. The perforation or alteration created typically penetrates through the stratum corneum layer, or both the stratum corneum layer and the epidermis, reducing or eliminating the barrier function of the stratum corneum. This will allow the administration of substances such as pharmaceuticals through the skin, or the removal of biomolecules, fluids or gases. There are several advantages to administering drugs in this fashion, for example: drugs can be administered continually on an out-patient basis over long periods of time, and the speed and/or efficiency of drug delivery can be enhanced for drugs which are either slow or unable to penetrate skin. Furthermore, this method of delivery provides an alternative delivery route for drugs that would otherwise require to be injected, eliminating the pain associated with needle punctures. Furthermore, the reduced barrier properties of the stratum corneum allow the taking of measurements of various fluid constituents, such as glucose, or to conduct measurements of gases.

Perforation involves the complete ablation of all layers of the stratum corneum to reduce or eliminate its barrier function. Ablation may also be characterized as partial when less than all layers of the stratum corneum are ablated, leaving sufficient tissue intact to substantially maintain. the barrier function. For the purpose of this application, "perforation" will mean only the complete ablation of all layers of the stratum corneum; "ablation" may mean, depending upon the context, either partial ablation or perforative ablation. Certain laser-induced alterations of molecules in the stratum corneum or interstitial spaces may also occur without actual ablation, and this will result in enhanced permeation of substances into or out of the body through the skin. A pulse or pulses of infrared laser irradiation at a subablative energy of, for example, 60 mJ per 2 mm spot, reduces or eliminates the barrier function of the stratum corneum and increases permeability without actually ablating or perforating the stratum corneum itself. The technique may be used for transdermal delivery of drugs or other substances, or for obtaining sample's of biomolecules, fluids or gases from the body. Different wavelengths of laser radiation and energy levels less than or greater than 60 mJ may also produce the enhanced permeability effects without ablating the skin.

For the purpose of this application, the terms "irradiation" or "alteration," or a derivative thereof, will generally mean perforation, ablation or modification which results in enhanced transdermal permeation of substances. The term "energized site" means the volume of tissue exposed to energy intended to enhance transdermal permeation of substances.

The mechanism for non-ablative alteration of the stratum corneum is not certain. It may involve changes in lipid or protein nature or function or from desiccation of the skin. Regardless, laser-induced alteration changes the permeability parameters of the skin in a manner which allows for increased passage of fluids and gases across the stratum corneum. This invention avoids the use of sharps such as needles, normally needed for drug administration or sample extraction. The absence of a contaminated sharp will eliminate the risk of accidental injury and its attendant risks to the health care worker, the patient, and anyone who may come into contact with the sharp, whether by accident or by necessity.

The absence of sharps also obviates the need for disposal of biologically hazardous waste. Thus, this invention provides an ecologically sound method of perforating or altering skin.

A typical laser can further be modified to include a container unit. Such a container unit can be added to: (1) increase the efficiency in the collection of fluids or gases; (2) reduce the noise created when the laser beam perforates the patient's tissue; and (3) collect the ablated tissue. The optional container unit is optionally evacuated to expedite the collection of the released materials such as the fluids or gases. The container can also be used to collect only ablated tissue. The noise created from the laser beam's interaction with the patient's skin may cause the patient anxiety. The optional container unit reduces the noise intensity and therefore alleviates the patient's anxiety and stress. The container unit also minimizes the risk of cross contamination and guarantees the sterility of the collected sample. The container also serves to attenuate and/or absorb any stray, potentially-hazardous electromagnetic radiation. The placement of the container unit in the use of this invention is unique in that it covers the tissue being punctured, at the time of puncture by the laser beam, and is therefore able to collect the fluid or gas samples and/or ablated tissue as the perforation or alteration occurs.

A typical laser used for this invention requires no special skills to use. It can be small, light-weight and can be used with regular or rechargeable batteries. The greater the laser's portability and ease of use, the greater the utility of this invention in a variety of settings, such as a hospital room, clinic or home.

Safety features can be incorporated into the laser that require that no special safety eyewear be worn by the operator of the laser, the patient, or anyone else in the vicinity of the laser when it is being used.

BRIEF DESCRIPTION OF THE DRAWINGS

The present invention may be better understood and its advantages appreciated by those skilled in the art by referring to the accompanying drawings, which are incorporated herein by reference. Although the drawings illustrate certain details of certain embodiments, the invention disclosed herein is not limited to only the embodiments so illustrated. The invention disclosed herein may have equally effective or legally equivalent embodiments.

FIG. 3 shows an alternative means of exciting a laser rod using a diode laser.

FIG. 4 shows an alternative focusing mechanism.

FIG. 6 shows a patch which can be used to sterilize the site of irradiation.

DETAILED DESCRIPTION

Figure 1:
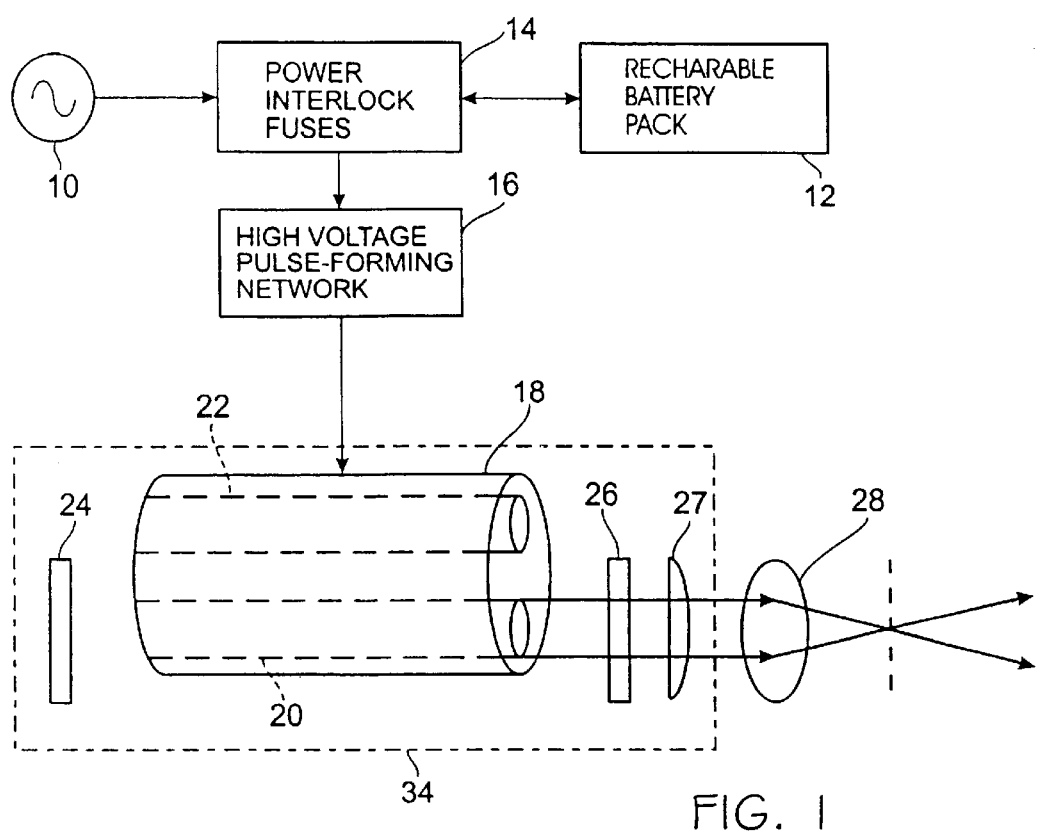
FIG. 1 shows a laser with its power source, high voltage pulse-forming network, flashlamp, lasing rod, mirrors, housing and focusing lens.

The invention described herein is not limited to the particular method steps, materials, configurations or terminology appearing herein. For example, unless the context indicates otherwise, singular forms include corresponding plurals, and vice versa. The claims of this invention are to be read to include any legal equivalent claim, or any portion thereof.

In most general terms, this invention provides a method of delivering at least one substance, such as a pharmaceutical, through the skin of a subject by means of administering an amount of energy to a portion of skin sufficient to enhance permeation at the energized site, at least as deep as the outermost surface of the stratum corneum, and contacting said energized site with said substance. Alternatively, the enhanced permeability following energy administration may provide for the enhanced collection of biomolecules, fluids or gases through the skin.

Although said skin site may be energized by energy selected fi7om the group consisting of chemical, mechanical, thermal, ultrasound and radiant energy (such as laser light), the primary embodiments described herein utilize a laser beam, specifically focused and lasing at an appropriate wavelength to create small perforations, ablations or alterations in the skin of a patient. The invention may include each type of energy source, capable of transmitting energy to the skin in the amounts and manner either reducing the electrical impedance of the skin or otherwise enhancing permeation. This includes any type of laser capable of transmitting such energy, including pulsed lasers, continuous wave lasers or those having appropriate modulation such as gating or Q-switching.

The laser beam is focused with a lens to produce an irradiated spot on the skin ranging in size from about 0.5 microns to about 5.0 cm in diameter. Optionally, the spot can be of any shape such as (for example) slit-shaped, with a width in the range of about 0.05 mm to 0.5 mm and a length of up to 2.5 mm.

Factors which should be considered in defining the laser beam (and the effectiveness of its characteristics) are wavelength, energy fluence, pulse temporal width and irradiation spot-size. Wavelength is determined by the laser material, such as Er:YAG; the preferred range of wavelengths is between about 1.5 and 10 microns. The preferred range of irradiation area on the skin is between about 0.1 to 10 mm in diameter. Energy fluence is a function of the laser energy output, in Joules, and the area of irradiation; the preferred range is between about 0.1 to 100,000 J/cm$^2$. Pulse temporal width is a consequence of the pulse width produced by a bank of capacitors, the flashlamp, and the laser rod material.

For some uses it is desirable to penetrate the skin in a manner which does not induce much (if any) blood flow. To perforate, ablate or alter the skin through the outer surface such as the stratum corneum layer, but not as deep as the capillary layer, the laser beam is focussed precisely on the skin, creating a beam diameter at the skin in the range of about 0.5 microns to 5.0 cm. The width can be of any size, being determined by the anatomy of the area irradiated together with the desired permeation rate of the substance to be applied, or the biomolecules, fluids or gases to be removed. The focal length of the lens can be of any length, but in one embodiment it is about 30 mm.

By altering wavelength, pulse length, energy fluence and irradiation spot size, it is possible to vary the effect on the stratum corneum between perforation, ablation and non-ablative alteration. Perforation, ablation and alteration of the stratum corneum results in enhanced inbound permeation of subsequently applied substances such as pharmaceuticals, or outbound permeation of biomolecules, fluids or gases.

For example, by reducing pulse energy but holding other variables constant, it is possible to change irradiative tissue-effects. To illustrate, using the Er:YAG laser (having a pulse length of about 300 microseconds with a single pulse of radiant energy) and irradiating a spot 2 mm in diameter on the skin, a pulse energy above approximately 100 mJ causes ablation, while many pulse energies below approximately 100 mJ result in non-ablative alterations to the stratum corneum. Optionally, by using multiple pulses, the threshold pulse energy required to enhance pharmaceutical delivery would be reduced by a factor approximately equal to the number of pulses.

Alternatively, by reducing the spot size, but holding other variables constant, it is possible to change irradiative tissue-effects. For example, halving the spot area will result in halving the requirement for energy to produce the same effect. Irradiation of spots having diameters down to about 0.5 microns can be obtained, for example, by coupling the radiant output of the laser into a microscope objective (e.g. as available from Nikon, Inc., Melville, N.Y.). In such a case, it is possible to focus the beam down to spots on the order of the limit of resolution of the microscope objective, which is perhaps on the order of about 0.5 microns. In fact, if the beam profile is Gaussian, the size of the affected irradiated area can be less than the measured beam size and can exceed the imaging resolution of the microscope. To non-ablatively alter tissue in this case, it would be suitable to use a 3.2 J/cm$^2$ energy fluence, which for a half-micron spot size, would require a pulse energy of about 6 nJ. This low a pulse energy is readily available from diode lasers, and can also be obtained from, for example, the Er:YAG laser by attenuating the beam by an absorbing filter, such as glass.

Similarly, by changing the wavelength of radiant energy, but holding other parameters constant, it is possible to change irradiative tissue-effects. For example, as a result of different radiant energy absorptive properties of tissues, using a Ho:YAG (holmium: YAG; 2.127 microns) in place of the Er:YAG (erbium: YAG; 2.94 microns) laser, would result in less absorption by the tissue of energy per unit volume, and less alteration.

Alternatively, these parameters can be changed to create a deeper penetration into the capillary layer. To perforate the skin to the capillary layer, the laser beam is focussed precisely on the skin, creating a beam diameter at the skin in the range of between about 0.1 mm and 1 mm, or optionally a slit-shaped beam ranging in width from between about 0.05 mm to 0.5 mm, and in length up to 2.5 mm. The focal length of the lens can be of any length, but in one embodiment it is 30 mm.

The laser is manipulated in such a way that a portion of the patient's skin is positioned at the site of the laser focus within the applicator. For fluid or gas collection, the location of the perforation is optimally at a site where the blood flow is high. Examples of such regions of the skin are on a fingertip, or the heel of a foot. With respect to alterations for delivery of anesthetics or other pharmaceuticals, or for immunization, a region of the skin which has less contact with hard objects or with sources of contamination is preferred. Examples are skin on the arm, leg, abdomen or back. Optionally, the skin heating element is activated at this time. Preferably a holder is provided with a hole coincident with the focal plane of the optical system. Optionally, a spring-loaded interlock 36 can be attached to the holder, so that when the patient applies a small amount of pressure to the interlock, to recess the holder to the focal point, a switch is closed and the laser will initiate a pulse of radiation. In this setup, the focal point of the beam is not in line with the end of the holder until that end is depressed. In the extremely unlikely event of an accidental discharge of the laser before proper positioning of the tissue at the end of the laser applicator, the optical arrangement will result in an energy fluence rate that is significantly low, thus causing a negligible effect on unintentional targets.

For certain purposes, it is useful to create multiple alterations of the skin simultaneously or in rapid sequence. To accomplish this, a beam splitter can optionally be added to the laser.

The technique may be enhanced by using a laser of a wavelength that is specifically absorbed by the skin components of interest (water, lipids or protein) that strongly affect the permeation. An alteration consisting of modifying the lipids in the stratum corneum may allow enhanced permeation while avoiding the higher energies which are more likely to affect the proteins and water.

Delivery of Anesthesia

A laser can be used to alter the skin through the outer surface, such as the stratum corneum layer, but not necessarily as deep as the capillary layer, to allow locally acting anesthetics to permeate the skin. Topically applied anesthetics must penetrate the stratum corneum layer in order to be effective. Presently, compounds acting as drug carriers are used to facilitate the transdermal diffusion of some drugs. These carriers sometimes alter the behavior of the drug, or are themselves toxic.

With the other parameters held constant, the intensity of the laser pump source will determine the intensity of the laser pulse, which will in turn determine the depth and extent of the resultant alteration. Therefore, various settings on the laser can be adjusted to allow penetration or modification of different thicknesses of stratum corneum.

Optionally, a beam-dump can be positioned in such a way as not to impede the use of the laser for perforation or alteration of extremities. The beam-dump will absorb any stray electromagnetic radiation from the beam which is not absorbed by the tissue, thus preventing any scattered rays from causing damage. The beam-dump can be easily removed for situations when the presence of the beam-dump would impede the placement of a body part on the applicator. This method of delivering anesthetic creates a very small zone in which tissue is irradiated, and only an extremely small zone of thermal necrosis (if any). An effective irradiation site can range from between about 0.1 min to 10 mm. in diameter, while a slit shaped site can range from between about 0.05 mm to 0.5 mm in width and up to approximately 2.5 mm in length. As a result, healing is quicker than (or as quick as) the healing after a skin puncture with a sharp implement. After irradiation, anesthetic can then be applied to the skin of the irradiation site using means of holding the anesthetic such as by formulations including gel material, viscous material (such as lotion or cream), patch material, dressing material or combinations thereof.

In one embodiment, said dressing material or patch material has a lower surface having electrically conductive gel, said gel for maintaining surrounding contact with at least some of said irradiated site. The substance to be delivered to the irradiation site may also be included in said gel. In another embodiment, said dressing material or patch material includes a lower surface having an electrically conductive semi-permeable membrane for maintaining surrounding contact with at least some of said irradiated site. The substance to be delivered to the irradiation site may also be included in said membrane. In a further embodiment, said dressing material or patch material is adapted as a conforming membrane to maintain optimal contact with an irregular terrain of said irradiated site.

In another form of the invention, said dressing material or patch material includes an upper layer having an outer surface and an inner surface, a lower permeable layer having an outer surface and an inner surface, said inner surface of said upper layer and said inner surface of said lower layer defining at least one enclosed intermediate chamber and dispensing means, said chamber having sufficient internal content to, upon dispensing from said chamber, exert positive outward pressure sufficient to assist the permeation of said substance. In another version of the invention, the content of at least one of said chambers includes the substance to be delivered to the irradiation site. Said dressing material or patch material layers may define a plurality of chambers and dispensing means, at least one of said chambers having sufficient internal content to, upon dispensing from said chamber, exert positive outward pressure sufficient to assist the permeation of the substance to be delivered to the irradiation site.

In another version, said dressing material or patch material layers further define, separate from said chamber, an enclosed intermediate reservoir with dispensing means, said reservoir having sufficient volume to contain said substance until dispensed. The invention may include a rupturable membrane separating said chamber and said reservoir, wherein the rupturing of said membrane allows the mixing of said contents of said chamber and reservoir.

Delivery of Other Substances

The present method can also be used to deliver a wide variety of other substances such as pharmaceuticals, in a manner similar to the above described delivery of anesthesia. By appropriate modification of the power level, and/or the spot size of the laser beam, alterations can be made which do not penetrate as deep as the capillary layer. These alterations can be made through only the outer surfaces, such as the stratum corneum layer or both the stratum corneum layer and the epidermis. Optionally an optical beam-splitter can be employed so that either single alterations or a number of alterations within a desired area can be made. After alteration, the pharmaceutical can then be applied to the skin of the irradiation site using means of holding the anesthetic such as by formulations including gel material, viscous material (such as lotion or cream), patch material, dressing material, or combinations thereof. Said substance may eventually be delivered by essentially direct contact with interstitial fluid of the subject.

The present method can be used in the delivery of a variety of substances, especially pharmaceuticals. Said substance may be selected from the group of in vivo diagnostic substances consisting of contrasting imaging agents, radionuclide based agents and mixtures thereof. Said substance may be selected from the group of systemically active substances consisting of neuroactive agents, auto acids, anti-hypertensives, anti-arrhythmics, hormones, chemotherapy antiparasitic agents, chemotherapy anti-microbial agents and mixtures thereof. Said substance may be selected from the group of locally active substances consisting of lidocaine, anesthetic agents, erectile dysfunction agents, metabolic inhibitors, steroidal or nonsteroidal anti-inflammatory agents, vitamins, retinoids, anticancer agents, antibodies, antibody conjugates and mixtures thereof. Said substance may be selected from the group consisting of protein based pharmaceutical substances, DNA based pharmaceutical substances, RNA based pharmaceutical substances and mixtures thereof, said protein based substance may be selected from the group consisting of cytokines, hormones, cell activation factors, cellular inhibitors, proteases, protease inhibitors, clotting factors and mixtures thereof. Said DNA or RNA based substance may be selected from the group consisting of oligonucleotides, gene therapy agents, ribozymes and mixtures thereof. Said substance may be selected from the group of antimicrobial chemotherapy agents consisting of anti-infectives, antifungals, antivirals and mixtures thereof. Said substance may be selected from the group of immunity generating substances consisting of vaccines, antigens, immunogen preparations and mixtures thereof. Said substance is selected from the group of permeation enhancing substances consisting of dimethylsulfoxide, alcohol, Azone, pentaerythritrol dioleat, lauramide DEA, polyethyleneglycol-10 laurate, nonoxynol-10, propylene glycol, urea, water, n-propanol, amines, amides, pyrrolidones, surfactants, fatty acids, liposomes and mixtures thereof.

For example nitroglycerin and antinauseants such as scopolamine; antibiotics such as tetracycline, streptomycin, sulfa drugs, kanamycin, neomycin, penicillin, and chloramphenicol; various hormones, such as parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, and angiotensin; steroid or non-steroid anti-inflammatory agents and systemic antibiotic, antiviral or antifungal agents. Alternatively, locally acting pharmaceuticals such as alprostadil, localized antibiotic, minoxidil, antiviral or antifungal agents or a chemotherapy or anti-cancer agent, can be delivered using this method. Protein or DNA based biopharmaceutical agents can also be delivered using this method.

Drugs may be applied by applying drug formulation directly to the irradiated skin site or by using a patch containing the drug. The patch may simply take the form of a viscous gel, lotion or ointment. Alternatively, the drug formulation may be incorporated into a laminate structure.

In one experiment, skin was lased alternatively at 2.94 Micron or 2.1 Micron wavelength using an Er:YAG (Venisect, Little Rock, Ark.) or Ho:YAG (Schwartz Electro-Optics, Orlando, Fla.) laser respectively. Pulse duration was 200–300 microseconds, the energy fluence delivered was between 4 and 10 J per square centimeter. A local anesthetic was then applied via a simple patch consisting of a Hill Top chamber (Hill Top Research, Loveland, Oreg.), or a self-forming patch (Dermaflex, Zila Pharmaceutical, Phoenix, Ariz.), or by dropping a small volume of liquid onto the site of irradiation. Anesthesia, as determined by insensitivity to needle-pricking or finger pinching, was achieved after five minutes in a region that extended at least 5 to 10 mm, or more, away from the irradiation site.

Alternatively, single or multiple reservoirs containing a drug between a matrix of semipermeable membrane and laminate could be applied. In the case of an unstable compound such as prostaglandin E1 (e.g. Caverject, Pharmacia & Upjohn, Kalamazoo, Mich.), lyophilized drug could be stored in one reservoir while the liquid components to be mixed with the drug could be stored in a separate reservoir, both separated by a membrane that may be ruptured by crushing or other physical means, thereby allowing the components to mix freely such that they would be available for dosing. This multi-reservoir concept may be further extended to include mixing of chemicals that will generate an electrical current, for the purpose of iontophoresis or electroporation.

Healing at the site of ablation will ultimately reduce the amount of drug that permeates over time. A substance may be included in the drug formulation or patch and applied to the site of irradiation whereby this substance slows the healing process or reduces the rate of scab formation thereby limiting the rate of closure of the permeation site and having the effect of extending the enhanced permeability characteristics of the lased site.

Immunization

As for delivery of pharmaceuticals, antigens can be administered through the skin for immunization purposes. The alterations are made through the outer layers of the skin, either singly or multiply, and the immunogen is provided in an appropriate formulation. For booster immunizations, where delivery over a period of time increases the immune response, the immunogen can be provided in a formulation which penetrates slowly through the alterations, but at a rate faster than possible through unperforated skin.

Delivery of Allergens

This method can also be applied to the delivery of allergens for example for allergy testing. Multiple alterations can be made through the outer layer of the skin, but not penetrating to the capillary level. A variety of allergens can then be applied to the skin, as in a skin patch test.

Drawing Biomolecules, Fluids or Gases

A laser can be used to perforate or alter the skin through the outer surface, such as the stratum corneum layer, but not as deep as the capillary layer, to allow the collection of biomolecules, fluids or gases. These substances may be used for a wide variety of tests. With the other parameters held constant, the intensity of the laser pump source will determine the intensity of the laser pulse, which will in turn determine the depth of the resultant ablation or alteration. Therefore, various settings on the laser can be adjusted to allow penetration of different thicknesses of skin.

Optionally, a beam-dump can be positioned in such a way as not to impede the use of the laser for ablation or alteration of extremities. The beam-dump will absorb any stray electromagnetic radiation from the beam which is not absorbed by the tissue, thus preventing any scattered rays from causing damage. The beam-dump can be easily removed for situations when the presence of the beam-dump would impede the placement of a body part on the applicator. This method of drawing fluids or gases creates a very small zone in which tissue is irradiated, and only an extremely small zone of thermal necrosis. A practical round hole can range from between about 0.1 mm to 1 mm in diameter, while a slit shaped hole can range from between about 0.05 mm to 0.5 mm in width and up to approximately 2.5 mm in length. As a result, healing is quicker or as quick as the healing after a skin puncture with a sharp implement. The fluid or gas can be collected into a suitable vessel, such as a small test tube or a capillary tube, or in a container unit placed between the laser and the tissue as described above. The process is non-contact and so neither the patient, the fluid or gas to be drawn, or the instrument creating the ablation or alteration is contaminated.

The technique of the present invention may be used to sample extracellular fluid in order to quantify glucose or the like. Glucose is present in the extracellular fluid in the same concentration as (or in a known proportion to) the glucose level in blood (e.g. Lonnroth P. Strindberg L. Validation of the "internal reference technique" for calibrating microdialysis catheters in situ. Acta Physiological Scandinavica 153(4):37580, 1995 April)

Figure 27:
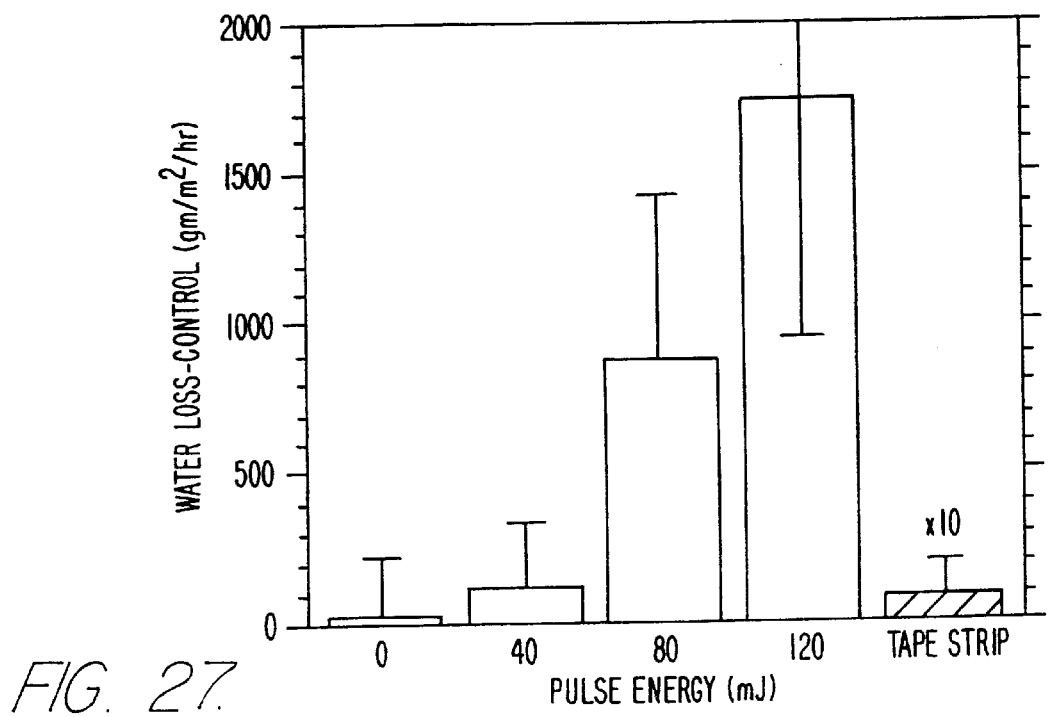
FIG. 27 shows that in volunteers irradiated with increasing laser energy fluence, there is a corresponding increase in transpidermal water loss. The tape strip data is just a positive control that proves that the measurement is indeed sensitive to increased skin water evaporation.

The ablation or alteration of the stratum corneum causes a local increase in the water loss through the skin (referred to as transepidermal water loss, or TEWL). As shown in FIG. 27, with increasing laser energy fluence ($J/cm^2$), there is a corresponding increase in water loss. The tape strip data is just a positive control that proves that the measurement is indeed sensitive to increased skin water evaporation.

Two of the energy fluences used to collect the data in FIG. 27 (e.g., 1.27 and 2.55 $J/cm^2$) are non-ablative and therefore show that non-ablative energies allow the alteration of the barrier function of stratum corneum thereby resulting in enhanced transepidermal water loss which can provide a diagnostic sample of extracellular water.

There are other things, besides glucose, that could be assayed in extracellular fluid. For example, HIV is present extracellularly and it is obvious that there is a benefit to obtaining samples for HIV analysis without having to draw blood with a sharp that could subsequently contaminate the health-care provider. Additionally, the present invention can be used to employ lasers non-ablatively to reduce or eliminate the barrier properties of non-skin barriers in the human body, such as the blood-brain interface, the floor of the third ventricle in the brain, and the sclera of the eye.

Alteration Without Complete Ablation

Subablative or partially ablative levels of laser energy may be applied to the skin which do not visibly harm the epidermis, but do result in a drop in skin electrical impedance at the lasing site. This results in an increase in skin permeability to various substances. This permeation may also be further enhanced by application of an electric current across the skin, providing a heretofore unexpected synergistic effect. This approach can be used to minimize damage to the skin as a result of applying large electrical currents while optimizing permeation, an important consideration for chronic applications of drugs and other substances transdermally.

There are advantages to the technique of altering the barrier functions of the stratum corneum without ablating it. The skin is altered, not ablated, so that its structural and biochemical makeup allows substances to more freely permeate. The consequence of this is four-fold: (1) the skin after irradiation still presents a barrier, albeit reduced, to external factors such as viruses and chemical toxins; (2) less energy is required than is required to ablate the stratum corneum, thus smaller and cheaper lasers can be used; (3) as compared to iontophoretic or electrophoretic drug delivery without irradiation of the skin, more drug may permeate using less electrical energy; and (4) healing at the site of alteration may take place more rapidly.

Laser Device

The practice of the present invention has been found to be effectively performed by various types of lasers; for example, the Venisect, Inc., Er:YAG laser skin perforator, or the Schwartz: Electro-Optical Ho.-YAG. Any pulsed or gated continuous wave laser producing energy that is strongly absorbed in tissue may be used in the practice of the present invention to produce the same result at a non-ablative wavelength pulse length pulse energy, pulse number, and pulse rate. Alternatively, if the laser energy is not strongly absorbed in the tissue, a dye that absorbs said energy can be placed on, in or under the skin.

As shown in FIG. 1, a typical laser comprises a power connection which can be either a standard electrical supply 10, or optionally a rechargeable battery pack 12, optionally with a power interlock switch 14 for safety purposes; a high voltage pulse-forming network 16; a laser pump-cavity 18 containing a laser rod 20, preferably Er:YAG; a means for exciting the laser rod, preferably a flashlamp 22 supported within the layer pump-cavity; an optical resonator comprised of a high reflectance mirror 24 positioned posterior to the laser rod and an output coupling mirror 26 positioned anterior to the laser rod; a transmitting focusing lens 28 positioned beyond the output coupling mirror; optionally a second focusing cylindrical lens 27 positioned between the output coupling mirror and the transmitting focusing lens; an applicator 30 for positioning the subject skin at the focal point of the laser beam, which is optionally heated for example with a thermoelectric heater 32, attached to the laser housing 34; an interlock 36 positioned between the applicator and the power supply; and optionally a beam dump 38 attached to the applicator with a fingertip access port 40.

Figure 2:
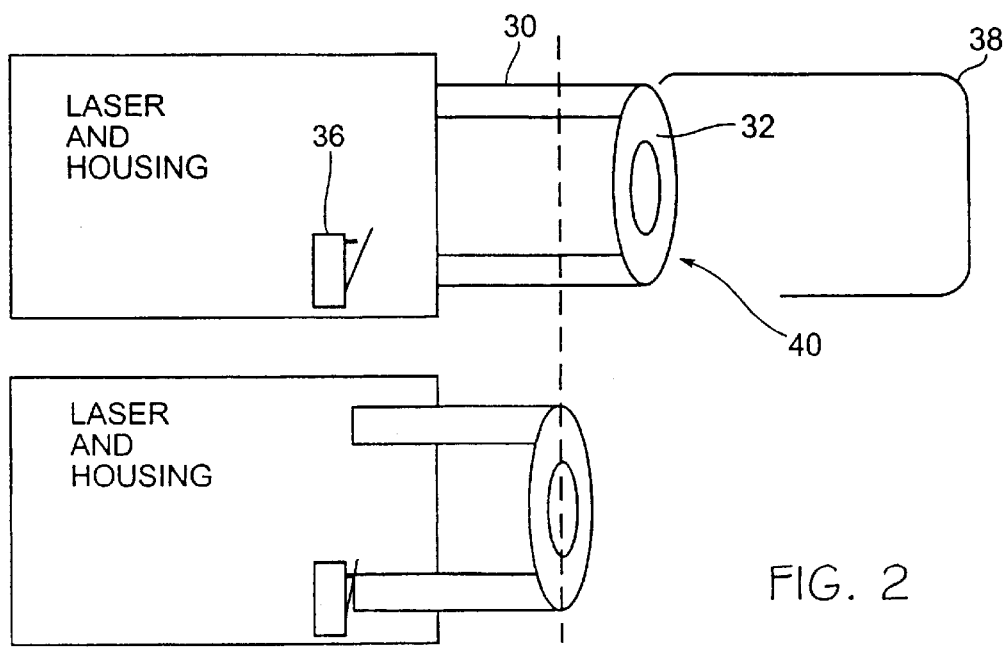
FIG. 2 shows an optional spring-loaded interlock and optionally heated applicator.

FIGS. 1–2 are diagrammatic representations of a typical laser that can be used for this invention. The laser typically draws power from a standard 110 V or 220 V line 10 (single phase, 50 or 60 Hz) which is rectified and used to charge up a bank of capacitors included in the high voltage pulse-forming network 16. Optionally, a rechargeable battery pack 12 can be used instead. The bank of capacitors establishes a high DC voltage across a high-output flashlamp 22. Optionally a power interlock 14, such as a key switch, can be provided which will prevent accidental charging of the capacitors and thus accidental laser excitation. A further interlock can be added to the laser at the applicator, such as a spring-loaded interlock 36, so that discharge of the capacitors requires both interlocks to be enabled.

With the depression of a switch, a voltage pulse can be superimposed on the already existing voltage across the flashlamp in order to cause the flashlamp to conduct, and, as a consequence, initiate the flash. The light from the flashlamp is located in the laser cavity 18 that has a shape such that most of the light is efficiently directed to the laser rod 20, which absorbs the light, and, upon de-excitation, subsequently lases. The laser cavity mirrors of low 26 and high 24 reflectivity, positioned collinearly with the long-axis of the laser rod, serve to amplify and align the laser beam.

Figure 12:
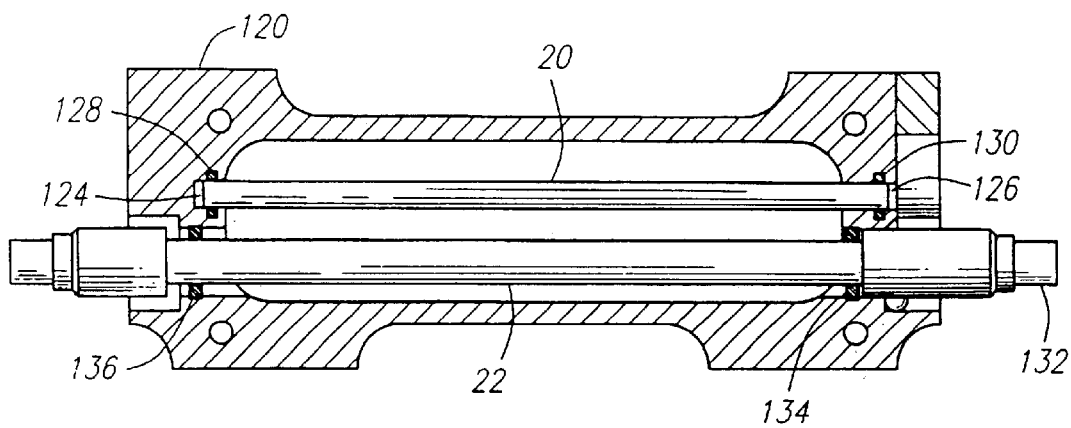
FIG. 12 shows an elastomeric mount for a solid state laser crystal element with optional mirrored surfaces applied to each end of the element.

Optionally, as shown in FIG. 12, the laser cavity mirrors comprise coatings 124, 126, applied to ends of the crystal element and which have the desired reflectivity characteristics. In a preferred embodiment an Er:YAG crystal is grown in a boule two inches in diameter and five inches long. The boule is core drilled to produce a rod in the range of between about 5 mm to 6 mm in diameter and about 5 inches long. The ends of the crystal are ground and polished. The output end, that is the end of the element from which the laser beam exits, is perpendicular to the center axis of the rod within 5 arc minutes. The flatness of the output end is $\frac{1}{10}$ a wavelength (2.9 microns) over 90% of the aperture. The high reflectance end, that is the end opposite the output end, comprises a two meter convex spherical radius. The polished ends are polished so that there are an average of ten scratches and five digs per Military Specification NEI-0-13830A. Scratch and dig are subjective measurements that measure the visibility of large surface defects such as defined by U.S. military standards. Ratings consist of two numbers, the first being the visibility of scratches and the latter being the count of digs (small pits). A #10 scratch appears identical to a 10 micron wide standard scratch while a #1 dig appears identical to a 0.01 mm diameter standard pit. For collimated laser beams, one normally would use optics with better than a 40-20 scratch-dig rating.

Many coatings are available from Rocky Mountain Instruments, Colorado Springs, Colo. The coating is then vacuum deposited on the ends. For a 2.9 micron wavelength the coatings for the rear mirrored surface 124 should have a reflectivity of greater than 99%. The coating for the output end surface, by contrast, should have a reflectance of between 93% and 95%. Other vacuum deposited metallic coatings with known reflectance characteristics are widely available for use with other laser wavelengths. The general equation which defines the reflectivity of the mirrors in a laser cavity necessary for the threshold for population inversion is:

$$R_1 R_2 (1-a_L)^2 \exp[(g^{21}-\alpha)2L]=1$$

where the R1 and R2 are the mirrors' reflectivities, $a_L$ is the total scattering losses per pass through the cavity, $g_2$, is the gain coefficient which is the ratio of the stimulated emission cross section and population inversion density, $\alpha$ is the absorption of the radiation over one length of the laser cavity, $g_{21}$ is the length of the laser cavity. Using the above equation, one can select a coating with the appropriate spectral reflectivity from the following references: Handbook of Optics, ch. 8, (W. Driscoll and W. Vaughan eds., McGraw-Hill: N.Y. 1978); 1 Handbook of Optics, ch. 35, (M. Bass, et al., eds., McGraw Hill, N.Y. 1995).

Optionally, as also shown in FIG. 12, the crystal element may be non-rigidly mounted. In FIG. 12 an elastomeric material o-ring 128 is in a slot in the laser head assembly housing 120 located at the high reflectance end of the crystal element. A second elastomeric material o-ring 130 is in a second slot in the laser head assembly at the output end of the crystal element. The o-rings contact the crystal element by concentrically receiving the element as shown. However, elastomeric material of any shape may be used so long as it provides elastomeric support for the element (directly or indirectly) and thereby permits thermal expansion of the element. Optionally, the flash lamp 22 may also be non-rigidly mounted. FIG. 12 shows elastomeric o-rings 134, 136, each in its own slot within the laser head assembly housing. In FIG. 12 the o-rings 134 and 136 concentrically receive the flash lamp. However, the flash lamp may be supported by elastomeric material of other shapes, including shapes without openings.

Optionally, as shown in FIG. 3, a diode laser 42 which produces a pump-beam collinear with the long-axis of the laser crystal can be used instead of the flashlamp to excite the crystal. The pump-beam of this laser is collimated with a collimating lens 44, and transmitted to the primary laser rod through the high reflectance infrared mirror 45. This high reflectance mirror allows the diode pump laser beam to be transmitted, while reflecting infrared light from the primary laser.

Our experiments have shown that energy can be delivered cumulatively beyond a threshold to achieve ablation. For example, five rapid pulses of 50 mJ each having a wavelength of 2.94 microns will achieve virtually the same ablative or alterative effect as a single 250 mJ pulse. This cumulative effect may be exploited with diode lasers. Laser diodes (such as supplied by SDL Corporation of San Jose, Calif.) will transmit a continuous beam of from 1.8 to 1.96 micron wavelength rad;ant energy. These diodes operate at up to 500 mW continuous wave (cw) output power and may be coupled by optical fibers to cumulatively produce higher energies useful for stratum corneum ablation. For example, one diode bar may contain ten such diodes, coupled to produce at least 5 W cw output. This power corresponds to 5 J/sec. cw energy which can then be gated by Q-switching or other mechanisms to produce pulsed energy of 5 mJ/msec. It has been shown that an ablative effect may be seen with as little as 100 mJ of energy delivered to a spot of about 1 mm. diameter. Four 25 millisecond pulses or a hundred 1 millisecond pulses from a diode laser of this type will thus have an ablative effect approximately equivalent to about one 100 mJ pulse in the same time period.

The Er:YAG lasing material is a preferred material for the laser rod because the wavelength of the electromagnetic energy emitted by this laser, 2.94 microns, is very near one of the peak absorption wavelengths (approximately 3 microns) of water. Thus, this wavelength is strongly absorbed by water and tissue. The rapid heating of water and tissue causes ablation or alteration of the skin.

Other useful lasing material is any material which, when induced to lase, emits a wavelength that is strongly absorbed by tissue, such as through absorption by water or nucleic acids or proteins or lipids, and consequently causes the required ablation or alteration of the skin. A laser can effectively cut or alter tissue to create the desired ablations or alterations where tissue exhibits an absorption coefficient in the range of between about 10 to 10,000 $cm^{-1}$. Examples of useful lasing elements are pulsed $CO_2$ lasers, Ho:YAG (holinium:YAG), Er: YAP, Er/Cr:YSGG (erbium/chromium: yttrium, scandium, gallium, garnet; 2.796 microns), Ho:YSGG (holmium: YSGG; 2.088 microns), Er:GGSG (erbium: gadolinium, gallium, scandium, garnet), Er:YLF (erbium: yttrium, lithium, fluoride; 2.8 microns), Tm:YAG (thulium: YAG; 2.01 microns), Ho:YAG (holmium: YAG; 2.127 microns); Ho/Nd:YA1O3 (holmium/neodymium: yttrium, aluminate; 2.85–2.92 microns), cobalt:$MgF_2$ (cobalt:magnesium fluoride; 1.75–2.5 microns), BF chemical (hydrogen fluoride; 2.6–3 microns), DF chemical (deuterium fluoride; 3.6–4 microns), carbon monoxide (5–6 microns), deep UV lasers, diode lasers and frequency tripled Nd:YAG (neodymium:YAG, where the laser beam is passed through crystals which cause the frequency to be tripled). The traits common to all such lasing elements, justifying inclusion of each such element in this group, are that they are all capable of transmitting energy to the skin in the amounts and manner necessary to either reduce the electrical impedance of the skin or otherwise enhance permeation.

Alternatively, if the laser energy is not strongly absorbed in the tissue, a dye that absorbs said energy can be placed on, in or under the skin.

Utilizing current technology, some of these laser materials provide the added benefit of small size, allowing the laser to be small and portable. In addition to Er:YAG, Ho:YAG or Er:YSGG lasers provide this advantage.

Figure 13:
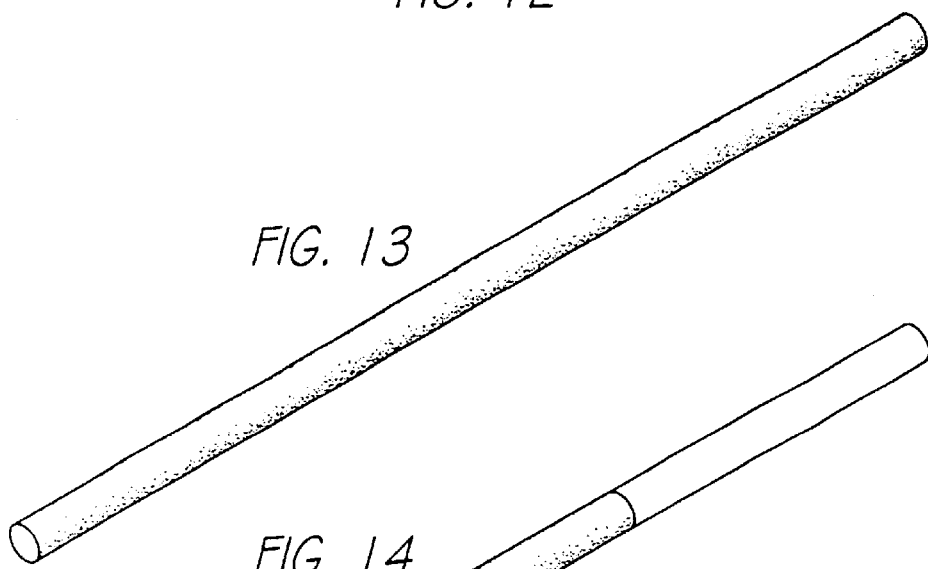
FIG. 13 shows an example of a crystal rod with matte finish around the full circumference of the entire rod.

Solid state lasers, including but not limited to those listed above, may employ a polished barrel crystal rod. The rod surface may also contain a matte finish as shown in FIG. 13. However, both of these configurations can result in halo rays which surround the central output beam. Furthermore, an all-matte finish, although capable of diminishing halo rays relative to a polished rod, will cause a relatively large decrease in the overall laser energy output. In order to reduce halo rays and otherwise affect beam mode, the matte finish can be present on bands of various lengths along the rod, each band extending around the entire circumference of the rod.

Figure 14:
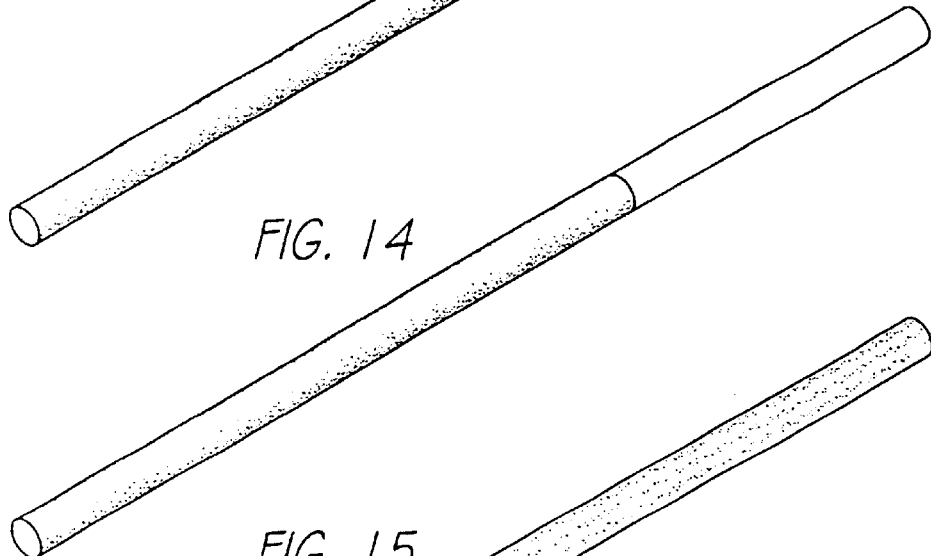
FIG. 14 shows an example of a crystal rod with matte finish around the full circumference of two-thirds of the rod.
Figure 15:
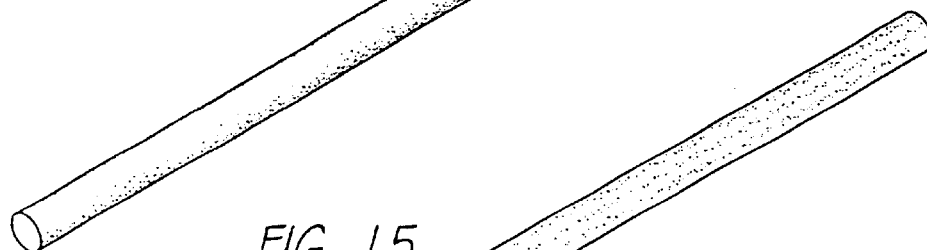
FIG. 15 shows an example of a crystal rod with matte stripes along its longitudinal axis.

Alternatively, the matte finish may be present in bands along only part of the rod's circumference. FIG. 14 shows a laser crystal element 142 in which the matte finish is present upon the full circumference of the element along two-thirds of its length. Alternatively, as shown in FIG. 15, matte stripes may be present longitudinally along the full length of the rod. The longitudinal stripes may alternatively exist along only part of the length of the rod, such as in stripes of various lengths. A combination of the foregoing techniques may be used to affect beam shape. Other variations of patterns may also be employed in light of the beam shape desired. The specific pattern may be determined based on the starting configuration of the beam from a 100% polished element in fight of the desired final beam shape and energy level. A complete matte finish element may also be used as the starting reference point.

For purposes of beam shape control, any surface finish of greater than 30 microinch is considered matte. A microinch equals one millionth (0.000001) inch. This is a common unit of measurement employed in establishing standard roughness unit values. The degree of roughness is calculated using the root-mean-square average of the distances in microinches above or below the mean reference line, by taking the square root of the mean of the sum of the squares of these distances. Although matte surfaces of greater than 500 microinch may be used to affect beam shape, such a finish will seriously reduce the amount of light energy that enters the crystal rod and thus cut the laser's energy.

To remove the beam halo, a matte area of approximately 50 microinch is present around the full circumference of an Er:YAG laser rod for two-thirds the length of the rod. The non-matte areas of the rod are less than 10 microinch. A baseline test of the non-matte rod can be first conducted to determine the baseline beam shape and energy of the rod. The matte areas are then obtained by roughing the polished crystal laser rod, such as with a diamond hone or grit blaster. The specific pattern of matte can be determined with respect to the desired beam shape and required beam energy level. This results in a greatly reduced beam halo. The rod may also be developed by core drilling a boule of crystal so that it leaves an overall matte finish and then polishing the desired areas, or by refining a partially matte, partially polished boule to achieve the desired pattern.

Figure 16:
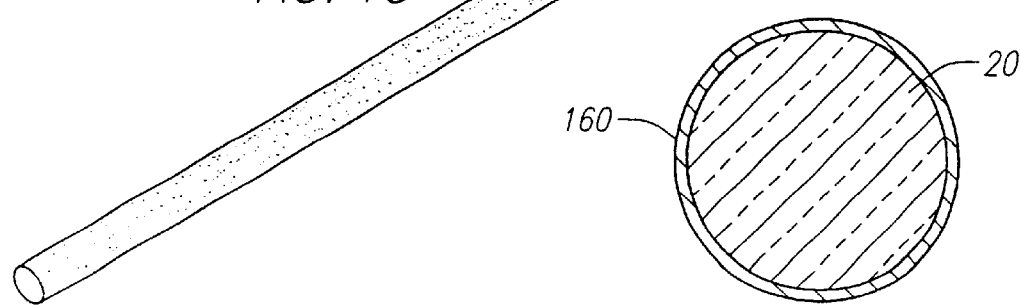
FIG. 16 shows a cross-section of a crystal laser rod element surrounded by a material having an index of refraction greater than the index of refraction of the rod.
Figure 17A:
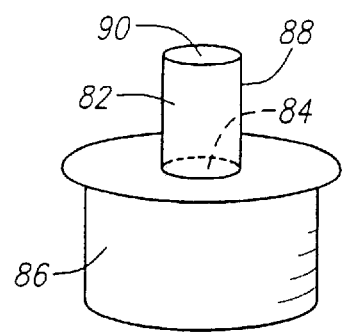
FIG. 17 shows various examples of a container unit.
Figure 17B:
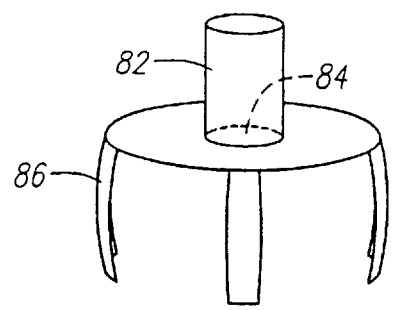
Figure 17C:
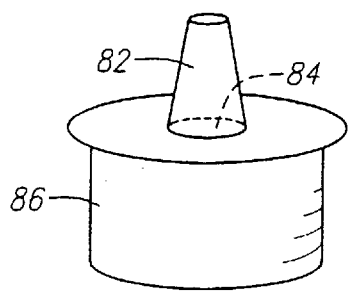
Figure 17D:
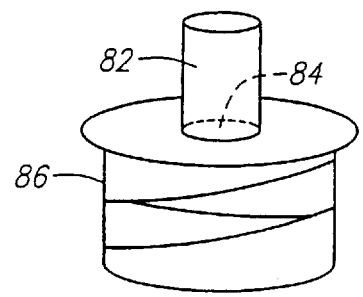
Figure 17E:
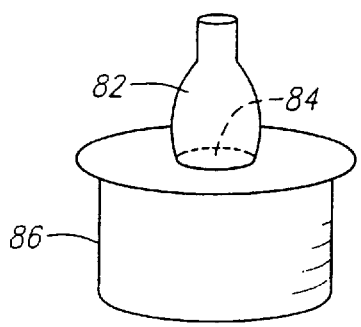
Figure 17F:
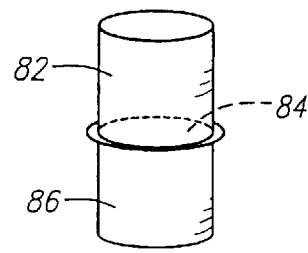
Figure 17G:
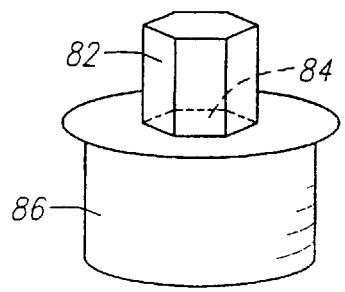

The beam shape of a crystal laser rod element may alternatively be modified as in FIG. 16 by surrounding the rod 20 in a material 160 which is transparent to the exciting light but has an index of refraction greater than the rod. Such a modification can reduce the halo of the beam by increasing the escape probability of off-axis photons within the crystal. This procedure may be used in place or in addition to the foregoing matte procedure.

The emitted laser beam is focused down to a millimeter or submillimeter sized spot with the use of the focusing lens 28. Consideration of laser safety issues suggests that a short focal length focusing lens be used to ensure that the energy fluence rate ($W/cm^2$) is low except at the focus of the lens where the tissue sample to be ablated or altered is positioned. Consequently, the hazard of the laser beam is minimized.

The beam can be focused so that it is narrower along one axis than the other in order to produce a slit-shaped ablation or alteration through the use of a cylindrical focusing lens 27. This lens, which focuses the beam along one axis, is placed in series with the transmitting focusing lens 28. When ablations or alterations are slit-shaped, the pain associated with the ablation or alteration is considerably reduced.

Optionally, the beam can be broadened, for instance through the use of a concave diverging lens 46 (see FIG. 4), prior to focusing through the focusing lens 28. This broadening of the beam results in a laser beam with an even lower energy fluence rate a short distance beyond the focal point, consequently reducing the hazard level. Furthermore, this optical arrangement reduces the optical aberrations in the laser spot at the treatment position, consequently resulting in a more precise ablation or alteration.

Figure 5A:
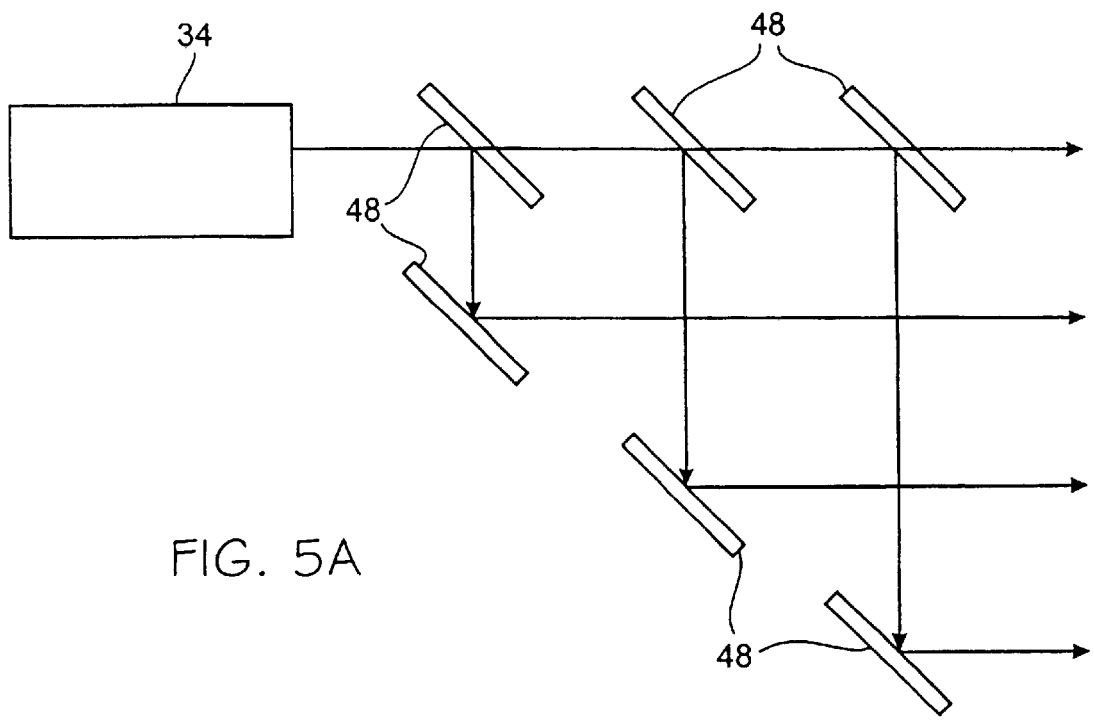
FIG. 5 shows optional beam splitters for creating multiple simultaneous perforations.
Figure 5B:
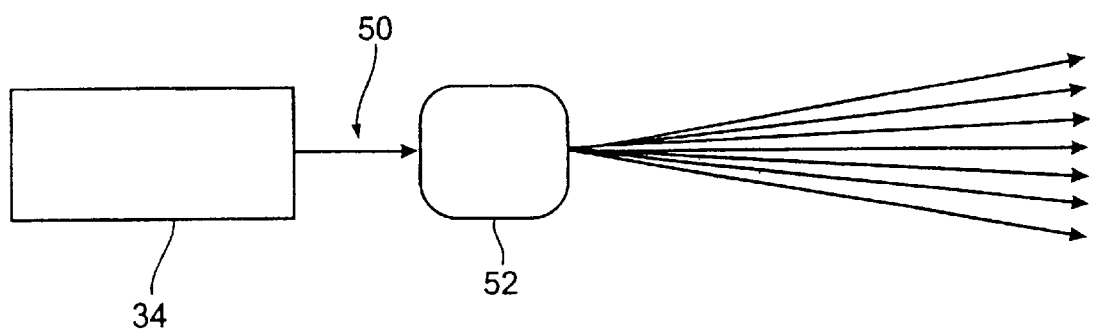

Also optionally, the beam can be split by means of a beam-splitter to create multiple beams capable of ablating or altering several sites simultaneously or near simultaneously. FIG. 5 provides two variations of useful beam splitters. In one version., multiple beam splitters 48 such as partially silvered mirrors, dichroic mirrors, or beam-splitting prisms can be provided after the beam is focused. Alternatively, an acousto-optic modulator 52 can be supplied with modulated high voltage to drive the modulator 52 and bend the beam. This modulator is outside the laser cavity. It functions by deflecting the laser beam sequentially and rapidly at a variety of angles to simulate the production of multiple beams.

Figure 8:
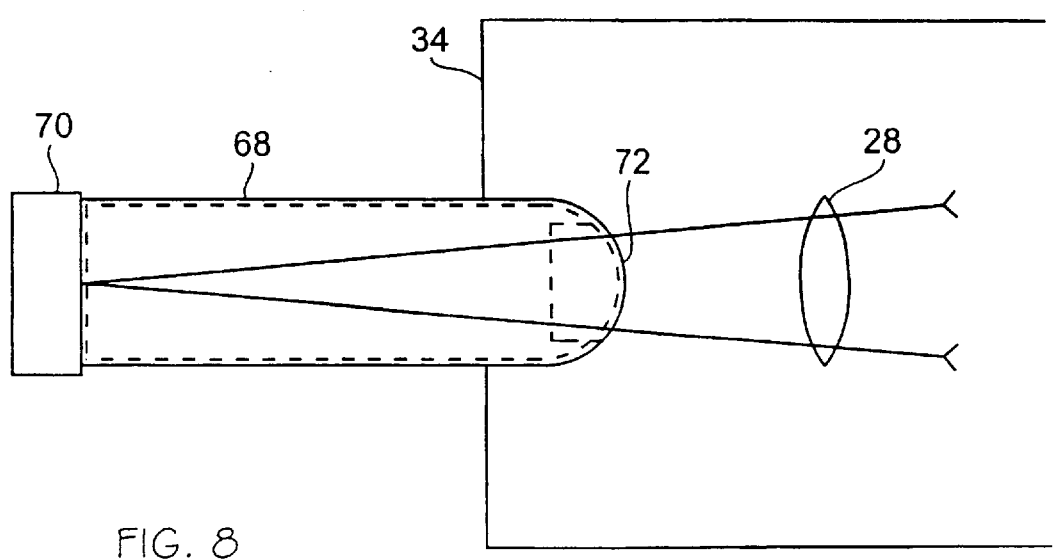
FIG. 8 shows an optional container unit for collecting fluids or gases, ablated tissue, and/or other matter released from the site of irradiation, and for reducing noise resulting from the interaction between the laser and the patient's tissue.

A container unit 68 is optionally fitted into the laser housing and is positioned proximal to the ablation or alteration site. The container unit reduces the intensity of the sound produced when the laser beam ablates or alters the patient's tissue, increases the efficiency of fluid or gas collection, and collects the ablated tissue and other matter released by the ablation. The container unit can be shaped so as to allow easy insertion into the laser housing and to provide a friction fit within the laser housing. FIG. 8 shows a typical container unit inserted into the laser housing and placed over the ablation site.

The container unit 68 comprises a main receptacle 82, including a lens 84. The main receptacle collects the fluid or gas sample, the ablated tissue, and/or other matter released by the ablation. The lens is placed such that the laser beam may pass through the lens to the ablation site but so that the matter released by the ablation does not splatter back onto the applicator. The container unit also optionally includes a base 86, attached to the receptacle. The base can optionally be formed so as to be capable of being inserted into the applicator to disengage a safety mechanism of the laser, thereby allowing the laser beam to be emitted.

As shown in FIG. 17, the shape and size of the container unit 68 are such as to a flow placement next to or insertion into the applicator, and to allow collection of the fluid or gas samples, ablated tissue, and/or other matter released by the ablation or alteration, Examples of shapes that the main receptacle may take include cylinders, bullet shapes, cones, polygons and free form shapes. Preferably, the container unit has a main receptacle, with a volume in the range of about 1 to 2 milliliters. However, larger and smaller receptacles will also work.

Figure 11:
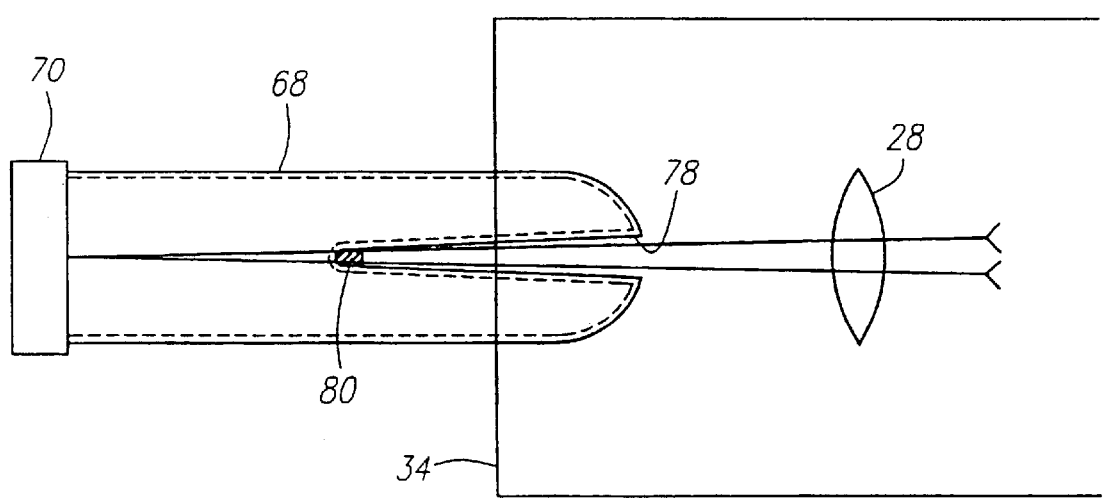
FIG. 11 shows an optional version of the collection container unit which is especially useful when the container unit includes a reagent for mixing with the sample.

The lens 84, which allows the laser beam to pass through while preventing biological and other matter from splattering back onto the applicator, is at least partially transparent. The lens is constructed of a laser light-transmitting material and is positioned in the pathway of the laser beam, at the end of the container unit proximal to the beam. The transmitting material can be quartz, but other examples of suitable infrared materials include rock salt, germanium, and polyethylene. As shown in FIG. 11, the lens may optionally include a mask of non-transmitting material 85 such that the lens may shape the portion of the beam that is transmitted to the ablation site.

The main receptacle 82 is formed by the lens and a wall 88, preferably extending essentially away from the perimeter of the lens. The open end of the main receptacle or rim 90 is placed adjacent to the ablation site. The area defined by the lens, wall of the main receptacle and ablation or alteration site is thereby substantially enclosed during the operation of the laser.

The base 86 is the part of the container unit that can optionally be inserted into the applicator. The base may comprise a cylinder, a plurality of prongs or other structure. The base may optionally have threading. Optionally, the base, when fully inserted, disengages a safety mechanism of the laser, allowing the emission of the laser beam.

Figure 18:
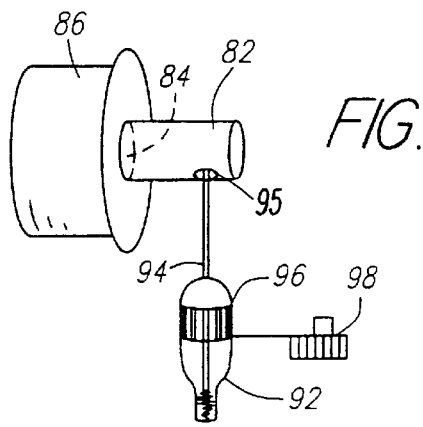
FIG. 18 shows a container unit with an additional vessel.
Figure 20:
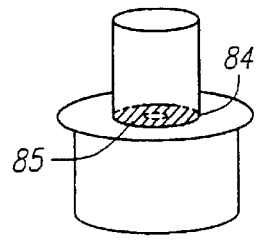
FIG. 20 shows an example of a lens with a mask.

As shown in FIG. 18, the container unit may also include an additional vessel 92 which collects a portion of the matter released as part of the ablation or alteration. For example, this vessel can collect liquid or particulate matter, while the main receptacle 82 collects any ablated tissue. The liquid or particulate matter may be channeled into the vessel through a capillary tube 94 or other tubing which extends fi7om the main receptacle into the vessel. The vessel is optionally detachable. The main receptacle may have a hole 95 in the wall through which the capillary tube or other tubing may be securely inserted. The vessel may have a removable stop 96 which sufficiently covers the open end of the vessel to prevent contamination with undesired material, but has an opening large enough for the capillary tube or other tubing to be inserted. The capillary tube or other tubing can extend outwardly from the main receptacle's wall and into the vessel through the removable stop. Once the sample has been collected, the stop may optionally be removed and discarded. The vessel may then optionally be seated with a cap 98 to prevent spillage. The vessel is preferably bullet shaped.

Additionally, the interiors of the main receptacle 82, the capillary tube 94 or other tubing, and/or the additional vessel 92 are optionally coated with anticoagulating and/or preservative chemicals. Examples of preservatives include ethylenediaminetetraacetic acid (EDTA) or sodium benzoate. Examples of anticoagulating chemicals are sodium heparin and sodium citrate.

A typical container unit can comprise a cylindrical main receptacle 82, a cylindrical base 86, and an at least partially transparent circular lens 84 in the area between the main receptacle and base. Optionally, the lens may include a mask which shapes the beam that ablates the tissue. The interior of the main receptacle is optionally coated with anticoagulating and/or preservative chemicals. The container unit can be constructed of glass or plastic. The container unit is optionally disposable.

The container unit may also include an additional vessel 92 and a capillary tube 94 extending outwardly from the main receptacle's wall 88 and into the vessel through a removable stop 96. The vessel may optionally have a cap 98 to seal the opening so as to prevent spillage. The interior of the main receptacle, the capillary tube, and/or the additional vessel may optionally be coated with anticoagulating and/or preservative chemicals. The container unit can be constructed of glass or plastic. The container unit, including the capillary tube and the additional vessel, are optionally disposable.

Figure 19A:
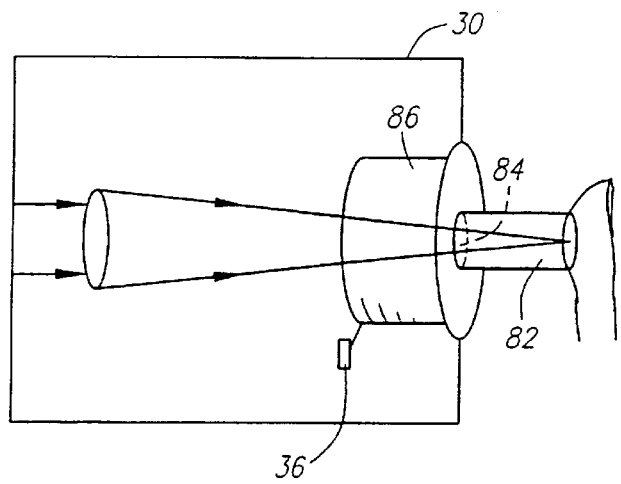
FIG. 19 shows examples of a container unit in use with a laser.
Figure 19B:
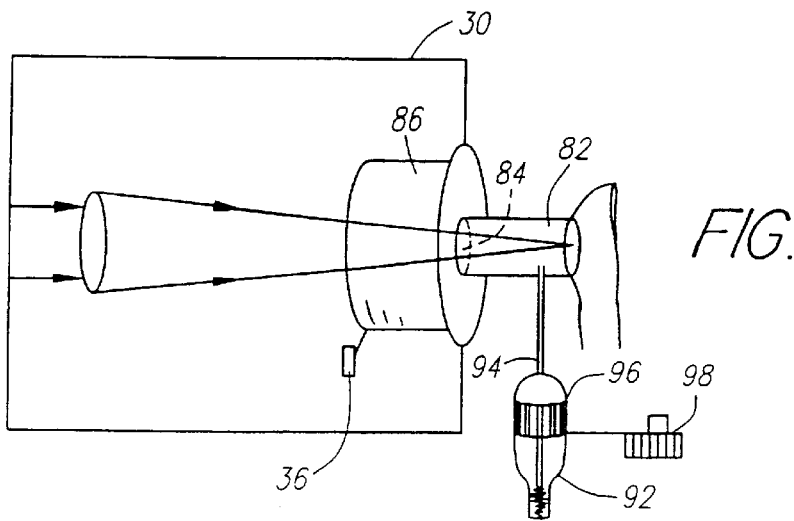

FIG. 19 shows examples of the use of a container unit with a laser for the purpose of drawing fluids or gases or to administer pharmaceuticals. In this embodiment, the applicator 30 is surrounded by the housing 34. The container unit is inserted in the applicator 30 and aligned so as to be capable of defeating the interlock 36. The base 86 of the container unit in this embodiment is within the applicator 30, while the rim 90 of the receptacle 82 is located adjacent to the tissue to be ablated. Optionally the additional vessel 92 can be connected by tubing 94 to the receptacle. The beam passes through the lens 84.

Figure 9:
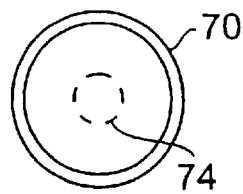
FIG. 9 shows a plug and plug perforation center.

Additionally, the container unit can be evacuated. The optional vacuum in the container unit exerts a less than ambient pressure over the ablation or alteration site, thereby increasing the efficiency in fluid or gas collection. The container unit is optionally coated with anticoagulating and/or preservative chemicals. The container unit's end proximal to the ablation or alteration site is optionally sealed air-tight with a plug 70. The plug is constructed of material of suitable flexibility to conform to the contours of the ablation site (e.g., the finger). The desired ablation or alteration site is firmly pressed against the plug. The plug's material is impermeable to gas transfer. Furthermore, the plug's material is thin enough to permit ablation of the material as well as ablation of the skin by the laser. The plug can be constructed of rubber. The plug perforation center 74, as shown in FIG. 9, is preferably constructed of a thin rubber material. The thickness of the plug is such that the plug can maintain the vacuum prior to perforation, and the laser can perforate both the plug and the tissue adjacent to the plug. For use with an Er:YAG laser, the plug should be in the range of between about 10 and 500 microns thick, but at the most 1 millimeter thick.

The plug perforation center 74 is large enough to cover the ablation or alteration site. Optionally, the ablated site is a round hole with an approximate diameter ranging from 0.1–1 mm, or slit shaped with a width in the range of between about 0.05 mm to 0.5 mm and an approximate length up to 2.5 mm. Thus, the plug perforation center is sufficiently large to cover ablation sites of these sizes.

The ablation or alteration site is firmly pressed against the rubber material. Optionally, an annular ring of adhesive can be placed on the rubber plug to provide an air-tight seal between the ablation site and the container unit. Preferably the ablation site on the plug is stretched when the tissue is pressed against the plug. This stretching of the plug material causes the hole created in the plug to expand beyond the size of the ablation or alteration created in the tissue. As a result, the fluid can flow unimpeded into the container unit 68. The laser beam penetrates the container unit, perforates; the plug perforation center 74 and ablates or alters the patient's tissue.

Figure 10:
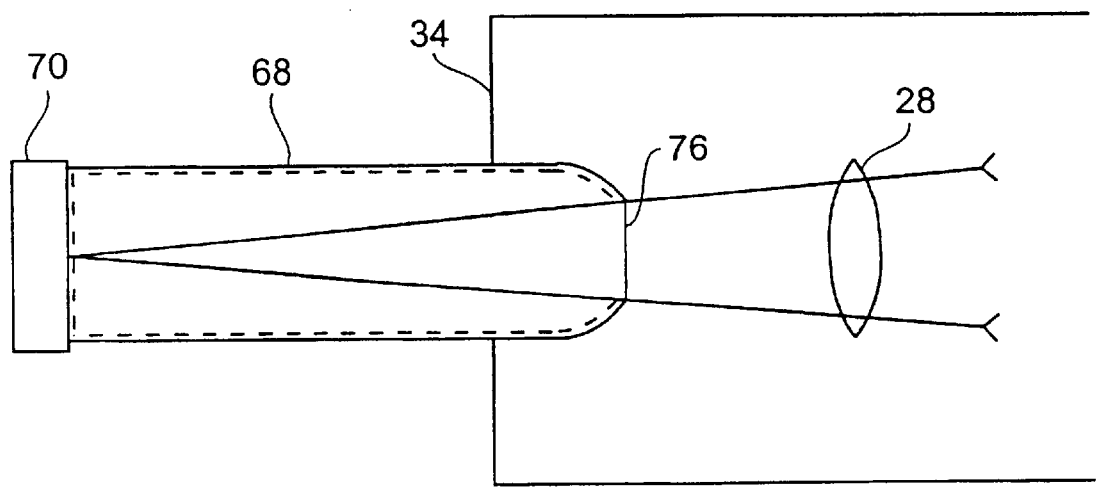
FIG. 10 shows an optional container unit for collecting ablated tissue, absorbing stray electromagnetic radiation, and reducing noise resulting from the interaction between the laser and the patient's tissue.

As shown in FIG. 10, the container unit 68 can include a hole 76 through which the laser passes, In this example, the container unit optionally solely collects ablated tissue. As in the other examples, the site of irradiation is firmly pressed against the container unit. The container unit can optionally include a plug proximal to the ablation site, however it is not essential because there is no need to maintain a vacuum. The container unit reduces the noise created from interaction between the laser beam and the patient's tissue and thus alleviate the patient's anxiety and stress. Optionally, the container unit is disposable, so that the container unit and plug can be discarded after use. Additionally, the main receptacle of the container unit, capillary tube and/or additional vessel can contain reagents for various tests to be performed on the collected fluid or gas. Examples of such reagents are sodium heparin and other reagents known in the art to be used in standard blood chemistry tests. See, for example, Garza D. et al., *Phlebotomy Handbook* (3d edition), Appleton and Lang Pub. Co., Norwalk, Conn., 1993, which is incorporated herein by reference. The reagents are positioned so that they will not be in the pathway of the laser light. The reagents are preferably present in a dry form, coating the interior walls of the collection part of the container unit, and thus readily available for interaction with the fluid sample as it is collected.

A preferable configuration for the container unit when it contains a reagent is shown in FIG. 11. In this configuration, the container unit has an indentation 78 at the base such that any fluid reagent present in the container unit will not fall into the line of fire of the laser beam when the container unit is held either vertically or horizontally. The apex 80 of the indented area is made of a infrared-transparent substance such as quartz.

When reagents are present in the container prior to collection of fluid or gas, it is beneficial to label the container unit in some manner as to the reagents contained inside, or as to the test to be performed on the sample using those reagents. A preferred method for such labeling is through the use of color-coded plugs. For example, a blue plug might indicate the presence of reagent A, while a red plug might indicate the presence of reagents B plus C within the container unit.

In order to sterilize the skin before ablation or alteration, a sterile alcohol- impregnated patch of paper or other thin material can optionally be placed over the site to be ablated. This material can also prevent the blowing off of potentially infected tissue in the plume released by the ablation. The material must be transparent to the laser beam. Examples of such material are a thin layer of quartz, mica, or sapphire. Alternatively, a thin layer of plastic, such as a film of polyvinyl chloride, can be placed over the skin. Although the laser beam will perforate the plastic, the plastic prevents most of the plume from flying out and thus decreases any potential risk of contamination from infected tissue. Additionally, a layer of a viscous sterile substance such as Vaseline can be added to the transparent material or plastic film to increase adherence of the material or plastic to the skin and further decrease plume contamination. Additionally, such a patch can be used to deliver allergens, local anesthetics or other pharmaceuticals as described below.

Figure 7A:
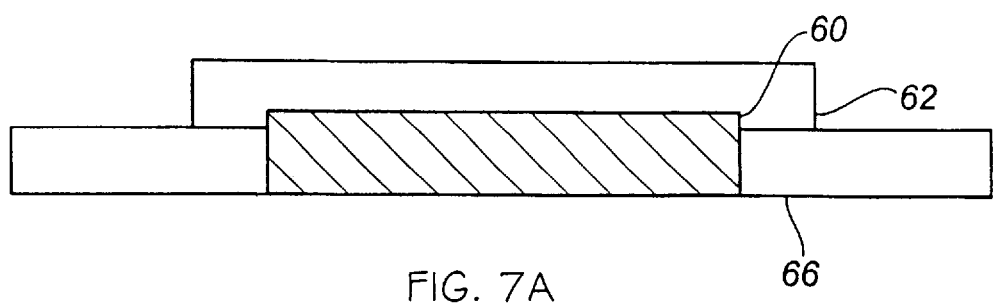
FIG. 7 shows alternative patches for sterilization and/or delivery of pharmaceuticals.
Figure 7B:
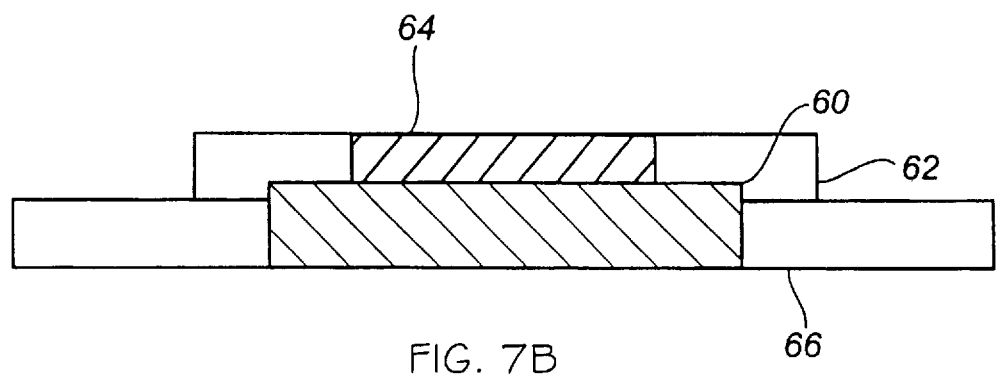

Examples of such a patch are provided in FIGS. 6 and 7. In FIG. 6, alcohol impregnated paper 54 is surrounded by a temporary adhesive strip 58. Side views of two alternative patches are shown in FIG. 7, where a sterilizing alcohol, antibiotic ointment, allergen, or pharmaceutical is present in the central region of the patch 60. This material is held in place by a paper or plastic layer 62, optionally with a laser-transparent material 64 such as mica, quartz or sapphire which is transparent to the laser beam at the center of the patch. The patch can be placed on the skin using an adhesive 66.

Modulated Laser

In addition to the pulsed lasers listed above, a modulated laser can be used to duplicate a pulsed laser for the purpose of enhancing topical drug delivery. This is accomplished by chopping the output of the continuous-wave laser by either modulating the laser output mechanically, optically or by other means such as a saturable absorber. (See, for example, "The Laser Guidebook", Jeff Hecht, McGraw-Hill, 1992). Examples of continuous-wave lasers include $CO_2$, which lases over a range between about 9 to 11 microns (e.g. Edinburgh Instruments, Edinburgh, UK), Nd:YAG, Thullium:YAG (Tm:YAG), which lases at 2.1 microns (e.g. CLR Photonics Inc., Boulder Colo.), or diode lasers which lase over a range of between about 1.0 to 2.0 microns (SDL Inc., San Jose, Calif.). The chopping of the laser output (for example, with a mechanical chopper from Stanford Research Instruments Inc., Sunnyvale, Calif.) will preferably result in discrete moments of irradiation with temporal widths in the range of between about a few tens of milliseconds down to microseconds. Alternatively, in the case of diode lasers (for example a diode laser emitting at 1.94 microns), the lasing process can be modulated by modulating the excitation current. A modulator for a laser diode power supply can be purchased from SDL Inc., San Jose, Calif. Alternatively, the continuous-wave beam can be optically modulated using, for example, an electro-optic cell (e.g. from New Focus Inc., Santa Clara, Calif.) or with a scanning mirror from General Scanning, Inc., Watertown Mass.

Electrical Impedance of the Skin

The stratum corneum shows two important electrical features. First, it becomes polarized as an electric field is continuously applied. Second, its impedance changes with the frequency of the applied electric field. The polarization effect may operate against the electric field applied, thus reducing the magnitude of effective current across the skin. Consequently, the efficiency of iontophoresis-facilitated transdermal delivery may be reduced with the duration of treatment. To minimize this effect, the current may be applied in a pulsatile manner. When the current is switched "on," charged molecules may be delivered iontophoretically through the skin. When the current is switched "off," the skin is allowed to depolarize. When the laser is used to alter the stratum corneum, the capacitance of the skin is reduced, thereby preventing the polarization effect that has limited applications of iontophoresis in the past.

The stratum corneum typically has an impedance on the order of 10 to 5000 Kohm×cm$^2$. Iontophoresis commonly utilizes a continuous current on the order of tens to hundreds of milliamperes, while electroporation may require even larger currents and voltages to drive molecules through this high resistance barrier. These currents require power sources that are driven by relatively large cumbersome power packs or batteries. These relatively high current requirements often result in burning of the skin.

By altering the stratum corneum, the skin resistance at the irradiation site is reduced by several orders of magnitude. Thus, much lower currents can be used to drive even large molecules across the skin. This allows for low voltage iontophoresis and electroporation whereby a small current, or a pulsed current, is used to drive small and large molecules through the site of irradiation and into the tissues, thereby minimizing power and current requirements as well as the risk of skin burning. One embodiment of the invention uses such electrical energy with a voltage in the range of between about 0.1 mV and 1.5 volts. In another embodiment, said electrical energy is in the range of between about 0.1 mV and 100 mV.

Where a single irradiation site is provided on the skin of a subject, an iontophoretic drug patch may be utilized where the voltage and current requirements are multi-fold less than without alteration. Because of this, more drug may be iontophoretically permeated into the tissues than without alteration. This effect is further enhanced by placing positive and negative electrodes at independent irradiated sites. Thus, the resistance of the complete circuit is orders of magnitude lower than that where there is no irradiation, or where only one site of irradiation has been made.

Experiments with laser irradiated stratum corneum show that 10-fold more drug can be pumped across the dermis using relatively minute voltages. Further, no decay in current was observed, even in samples that were iontop4oresed for five or more hours, demonstrating that there was no skin polarization effect. This indicates that a pulsed current is not a requirement for efficiently permeating molecules across irradiated skin, as it is with unirradiated skin. Note, however, that pulsed current could still be used, or alternatively, current that occasionally and only briefly reverses polarity in order to free permeating molecules that are bound up in the skin matrix.

Reduction of energy requirements resulting in enhanced permeation allows for a greater variety of mechanisms for delivering substances to the irradiation site. Means for delivering substances such as pharmaceuticals to or through the irradiation site may be selected from the group consisting of diffusion, thermal energy, electrical energy, mechanical displacement and combinations thereof. Enhanced permeability of the stratum corneum or the permeating molecules makes passive or assisted diffusion more effective. Similarly, relatively small amounts of electrical or thermal energy may accomplish effective permeation. This is especially true when permeation is facilitated by an electrical gradient on the skin generated by means selected from the group consisting of electrophoresis, iontophoresis and electroporation. Said delivery means may further include a source of electricity selected from the group consisting of an external electric current generator, a transportable battery, a solar powered generator, an electrochemical generator, a thermal energy generator, and a piezoelectric generator. Since such small amounts of energy are needed, body heat may be a sufficient source of thermal energy. A transportable battery may also be incorporated within said dressing material or patch material.

EXAMPLES

The following examples describe some methods and effects of administering energy to the skin of a subject, such as by the use of a laser, to increase the permeability of the stratum corneum for the purpose of delivering substances such as pharmaceuticals, or for drawing biomolecules, fluids or gases. These examples are not meant to limit the scope of the invention, but are merely alternative embodiments.

Example 1

An infrared laser radiation pulse was formed using a solid state, pulsed, multimode Er:YAG laser consisting of two flat resonator mirrors, an Er:YAG crystal as an active medium, a power supply, and a means of focusing the laser beam. The wavelength of the laser beam was 2.94 microns. The duration of the pulse was approximately 300 microseconds. The spot size was approximately 2 mm. Pulse energy used was 40, 80 or 120 mJ. Single pulses were used. Transepidermal water loss (TEWL) measurements were taken of the volar aspect of the forearms of human volunteers. Subsequently the forearms were positioned at the focal point of the laser, and the laser was discharged. Subsequent TEWL measurements were collected from the irradiation sites, and from these the measurements of unirradiated controls were subtracted. The results (shown in FIG. 27) show that at pulse energies of 40, 80 and 120 mJ, the barrier function of the stratum corneum was reduced and the resulting water loss was measured to be 131, 892 and 1743 g/m2/hr respectively.

The tape strip positive control (25 pieces of Scotch Transpore tape was serially applied and quickly removed from a patch of skin) was measured to be 9.0 gm/m$^2$/hr, thus the laser is more efficient at reducing the barrier function of the stratum corneum than tape-stripping.

Clinical assessment was conducted 24 hours after irradiation. Only a minor transient color change was apparent on the site lased at high energy, and no edema was present. None of the patients experienced irritation or required medical treatment.

Example 2

An infrared laser radiation pulse was formed using a solid state, pulsed, multimode Er:YAG laser consisting of two flat resonator Mirrors, an Er:YAG crystal as an active medium, a power supply, and a means of focusing the laser beam. The wavelength of the laser beam was 2.94 microns. The duration of the pulse was about 300 microseconds. The spot size was about 2 mm in diameter. A pulse energy used was about 60 mJ. A single pulse was used.

The volar aspect of the forearm was placed at the focal point of the laser, and the laser was discharged. After discharge of the laser, the irradiated site was treated with a 30% liquid lidocaine solution for two minutes. A 26G–0.5 needle was inserted into the laser irradiated site with no observable pain. Additionally, after a 6 minute anesthetic treatment, a 22G-1 needle was inserted into the laser irradiated site with no observable pain. The volunteers experienced no irritation and did not require medical treatment.

Example 3

Ablation threshold energy: normally hydrated (66%) stratum corneum (sc) was sandwiched between two microscope cover slides, and exposed to a single pulse of irradiation from the Er:YAG laser. Evidence of ablation was determined by holding the sample up to a light and seeing whether any stratum corneum was left at the irradiated site. From this experiment, it was determined that the irradiation threshold energy was in the range of between about 90 to 120 mJ. The threshold may be different when the sc is still overlying epidermis, as in normal skin., since it takes energy to remove the sc from the epidermis, to which it is adherent.

Example 4

Differential Scanning Calorimetry (DSC)

Figure 28:
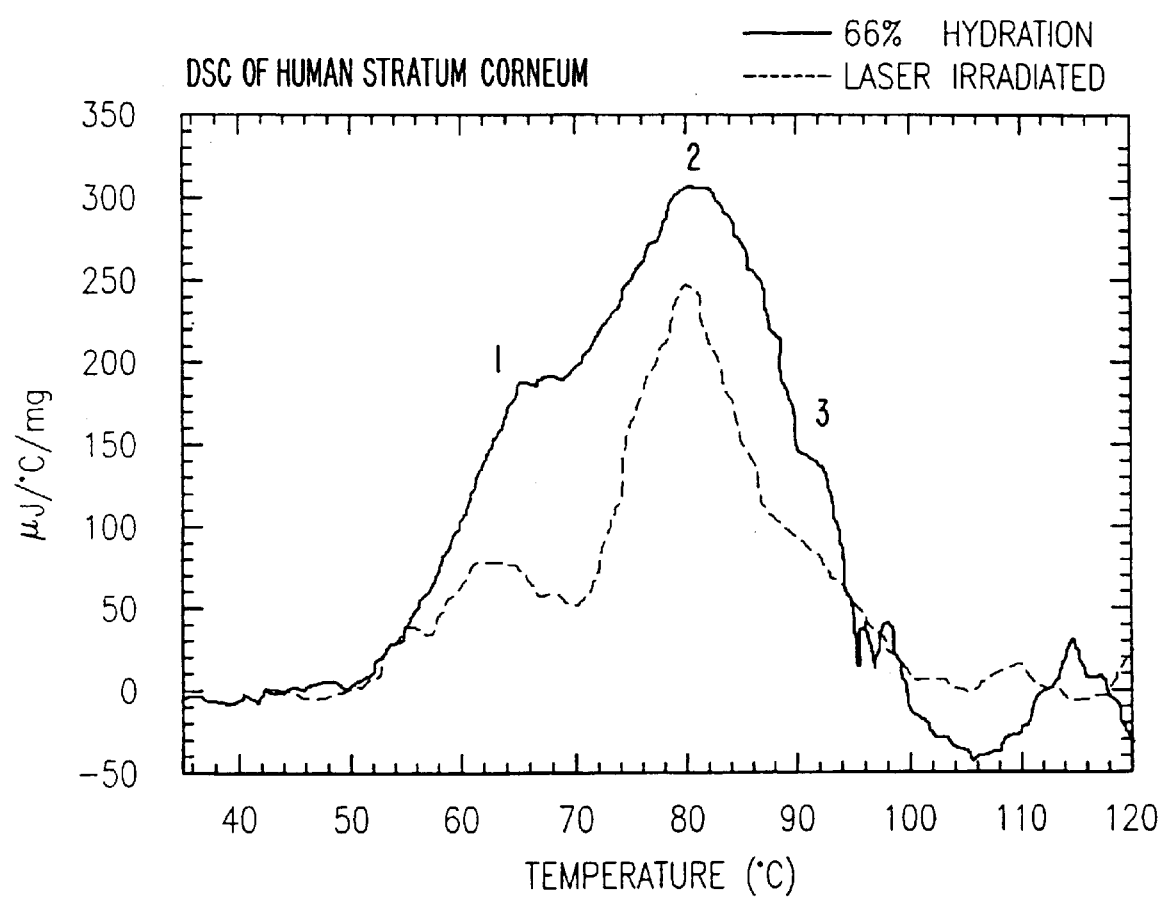
FIG. 28 is a chart showing a Differential Scanning Calorimetry (DSC) scan of normally hydrated (66%) human stratum corneum (sc), and a scan of Er:YAG laser irradiated sc using a subablative pulse energy of 60 mJ.
Figure 29:
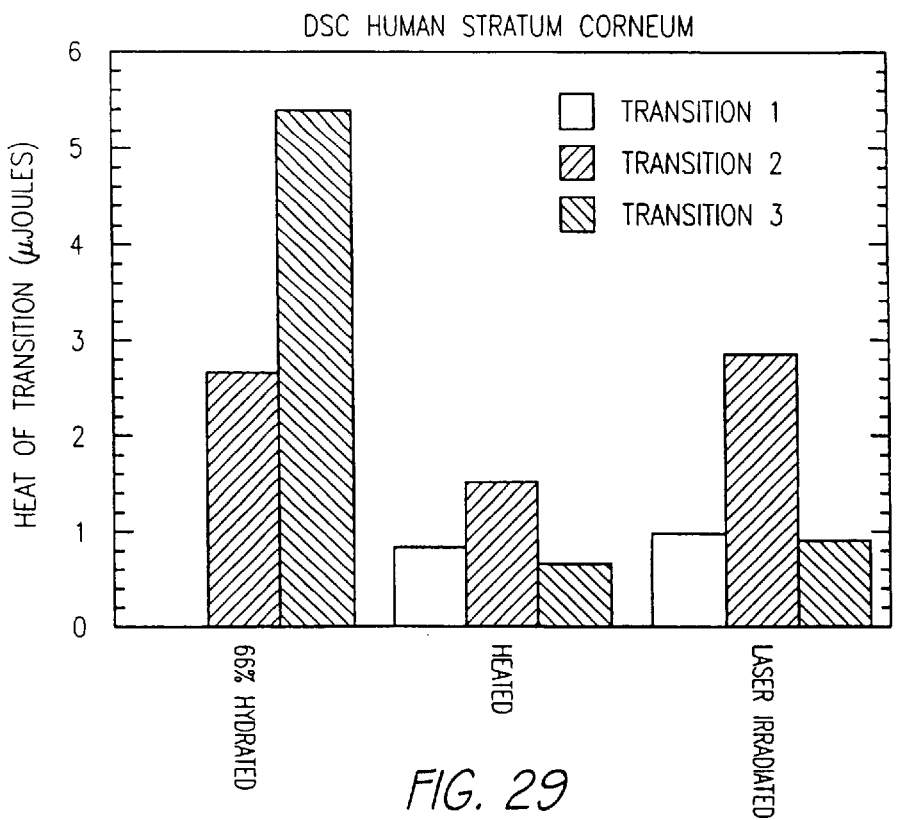
FIGS. 29–31 are charts showing the heat of transition ($\mu J$), center of the transition (° C. and the full-width at half-maximum of-the transition (° C.) for the scans of FIG. 28 as well as a scan of sc treated other ways (not shown in FIG. 28).
Figure 30:
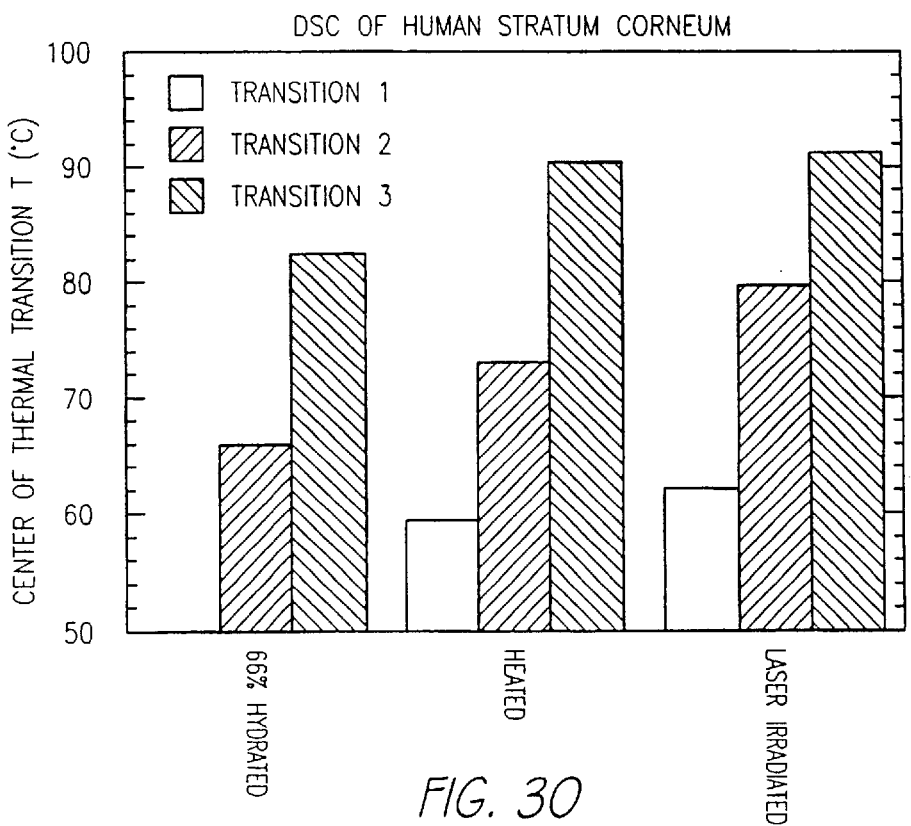
Figure 31:
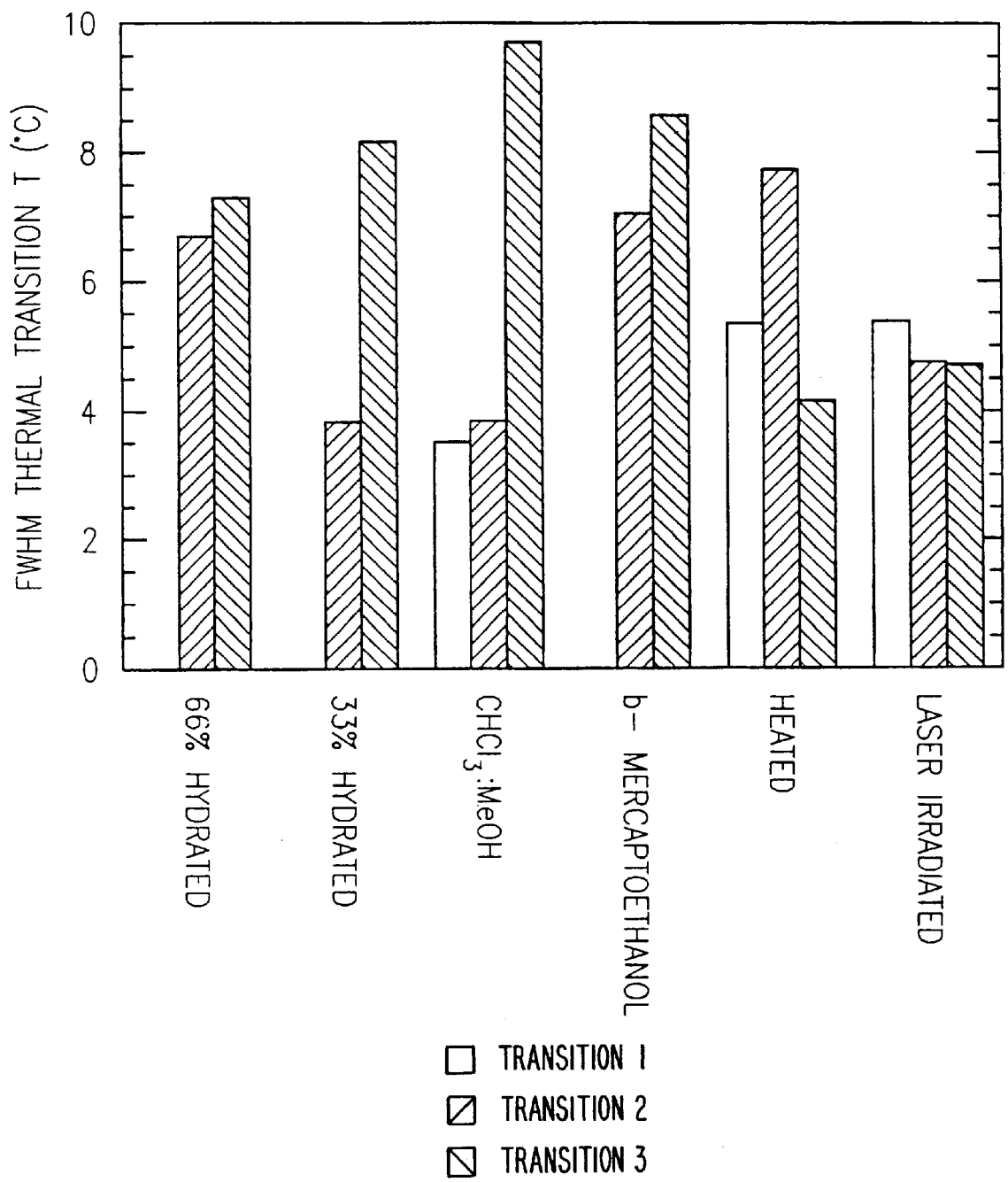

FIG. 28 shows a DSC scan of normally hydrated (66%) human sc, and a scan of Er:YAG laser irradiated sc using a subablative pulse energy of 60 mJ. Clearly there is a difference in the scans. Defining the thermal transition peaks at approximately 65° C., 80° C. and 92° C. (labelled as 1, 2 or 3, respectively), we determined the heat of transition ($\mu$J), center of transition (° C.) and the full-width at half-maximum of the transition (° C.). (See FIGS. 29–31). The results shown are on normal (66%) hydrated sc, dehydrated (33%) sc, water heated sc, Er:YAG laser irradiated sc, or sc that was immersed in chloroform-methanol (a lipid solvent) or beta-mercaptoethanol (a protein denaturant). The effect of laser irradiation on sc is consistent (depending on which transition you look at, 1, 2 or 3) with changes seen due to thermal damage (i.e. heated with steam), and de-lipidization. Permeation with $^3H_2O$ and transepidermal impedance experiments on skin treated the same way showed that these treatments (heat, solvent or denaturant) resulted in increased permeation (data not shown). Thus, the changes induced in the stratum corneum with these treatments, changes which are consistent with those seen in laser irradiated sc, and changes which do not result in sc ablation, result in increased permeation.

Example 5

Fourier Transform Infrared (FTIR) Spectroscopy

Figure 32:
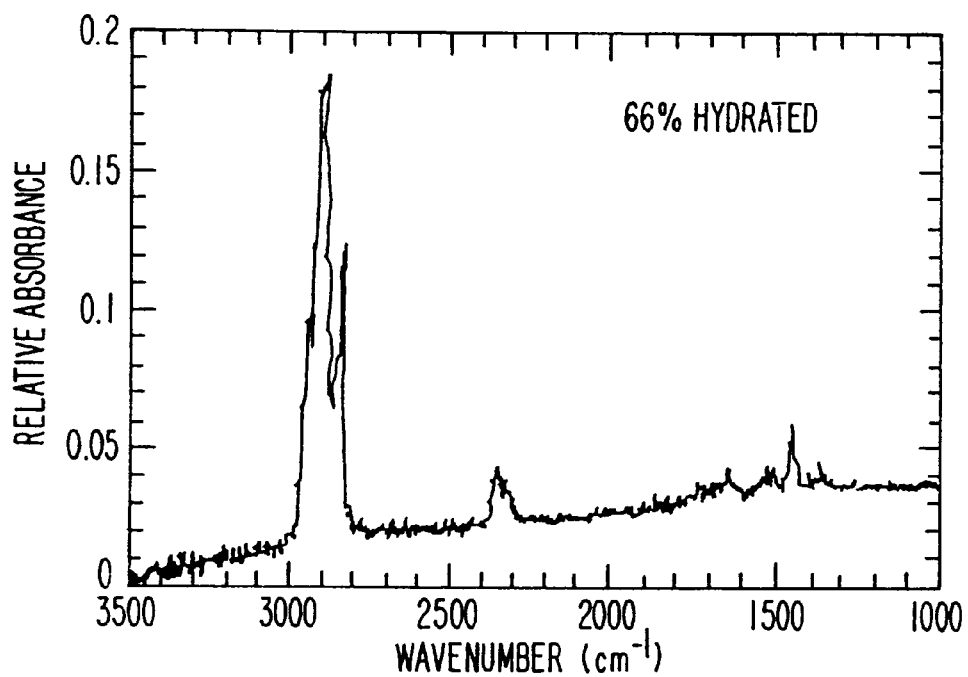
FIGS. 32–33 are charts of Fourier Transform Infrared ("FTIR") spectra showing that absorption bands that are due to water, proteins and lipids, change when the sc is irradiated.
Figure 33:
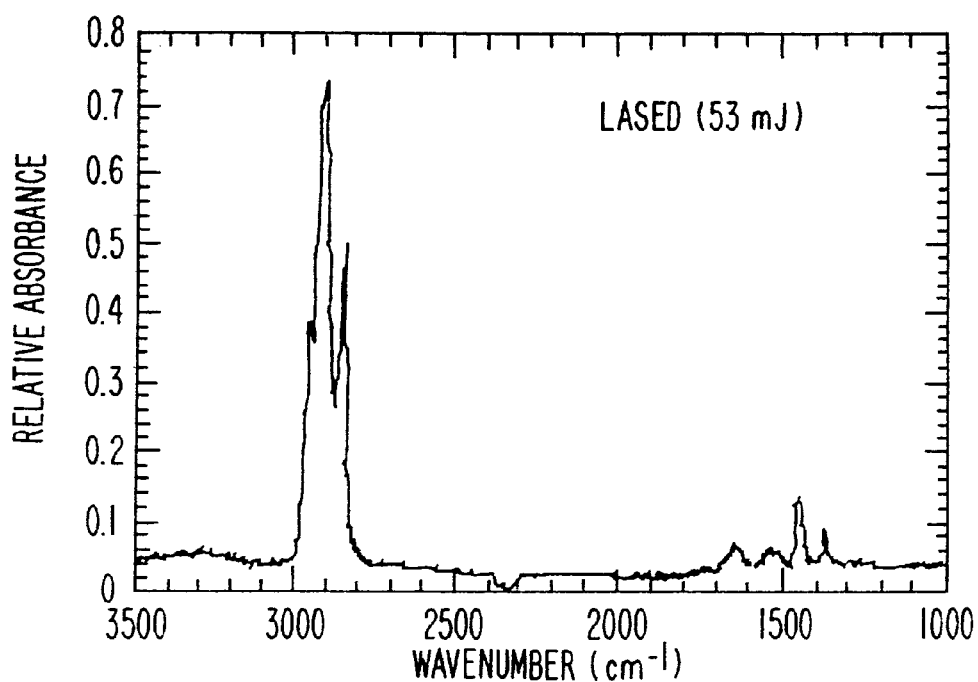
Figure 34A:
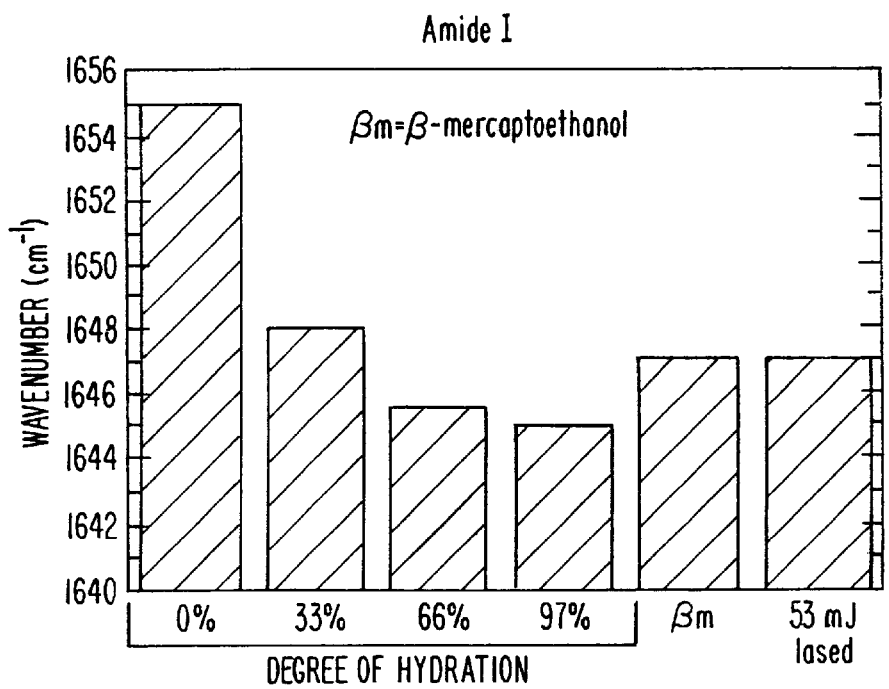
FIG. 34 shows that Amide I and II bands, which are due to the presence of proteins shift to larger wavenumber, consistent with what happens when skin is exposed to desiccation (in the case of Amide II), or desiccation and beta-mercaptoethanol (in the case of Amide I) do.
Figure 34B:
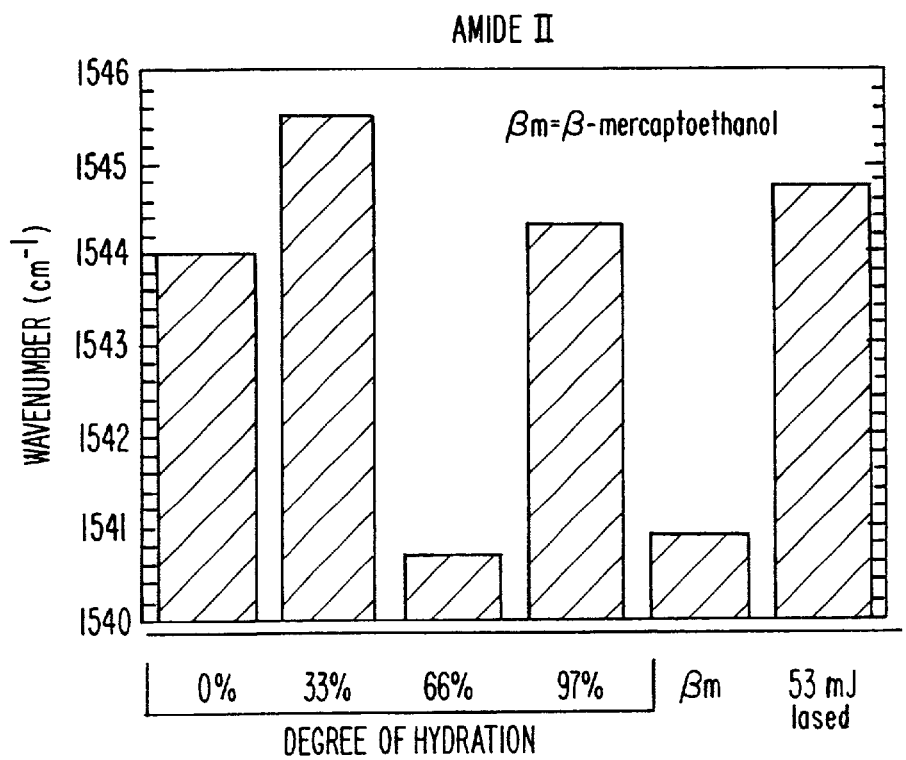
Figure 35A:
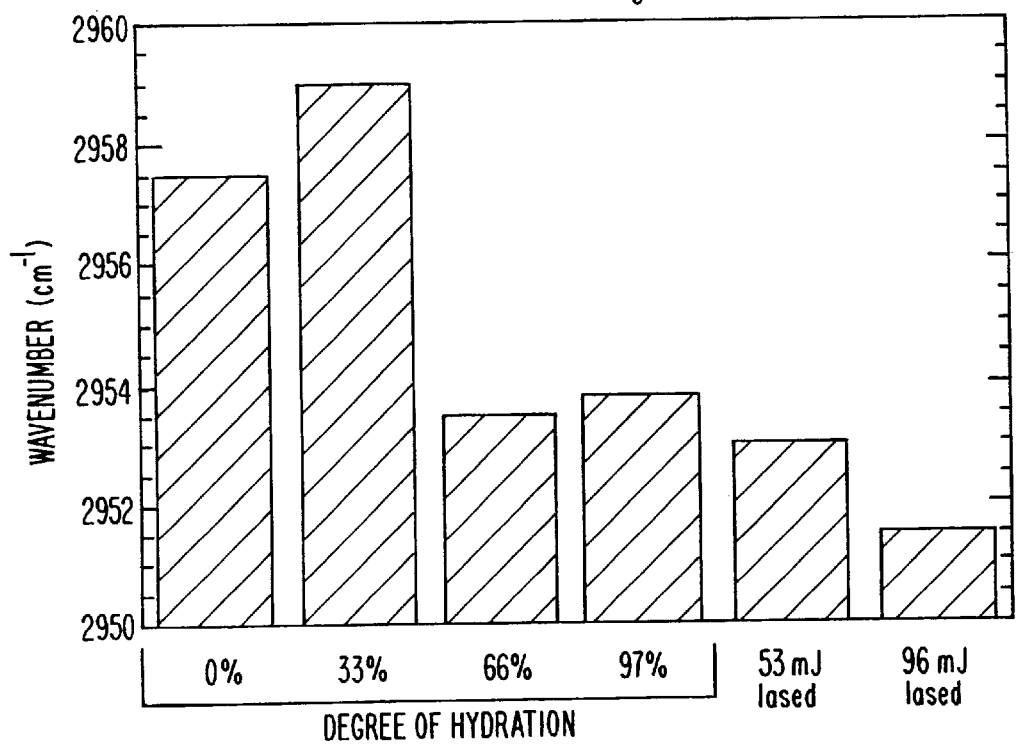
FIG. 35 shows that CHx vibrations may shift to a smaller wave number indicating that either the intermolecular association between adjacent lipid molecules has been disturbed and/or the environment around the lipid molecules has changed in such a way so that the vibrational behavior of the molecules changes.
Figure 35B:
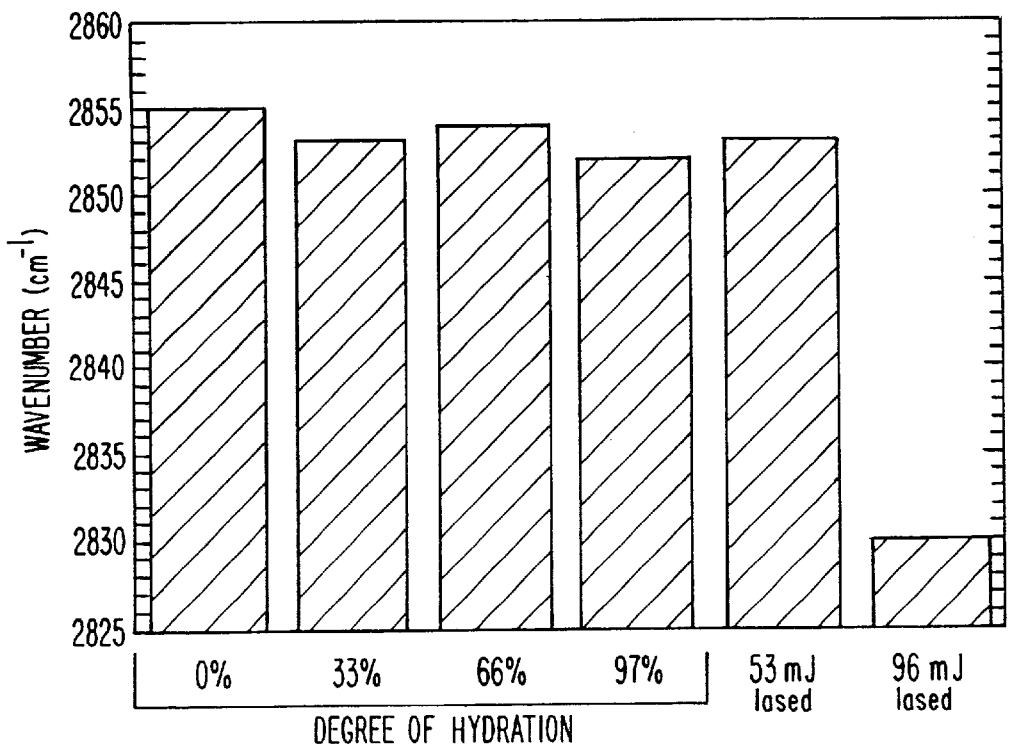

FTIR spectroscopy was used to study sc treated the same way as in the DSC experiments, except the energy used was between about 53 and 76 mJ. Detailed analysis of the spectra (see, FIGS. 32–33) show that absorption bands that are due to water, proteins and lipids change when the sc is irradiated. Some of these changes are consistent with changes seen during non-laser treatment of the sc (e.g. desiccation, thermal damage, or exposure to lipid solvents or protein denaturants). For example, the Amide I and II bands, which are due to the presence of proteins (most likely keratin, which makes up the bulk of protein in sc), shift to a larger wave number, consistent with what desiccation (in the case of Amide II) or desiccation and beta-mercaptoethanol (in the case of Amide I) do (see, for example, FIG. 34). The $CH_x$ vibrations (due to bonds in lipids) may shift to a smaller wave number indicating that either the intermolecular association between adjacent lipid molecules has been disturbed and/or the environment around the lipid molecules has changed in such a way that the vibrational behavior of the molecules changes (see, e.g., FIG. 35).

Example 6

Histology

Figure 36:
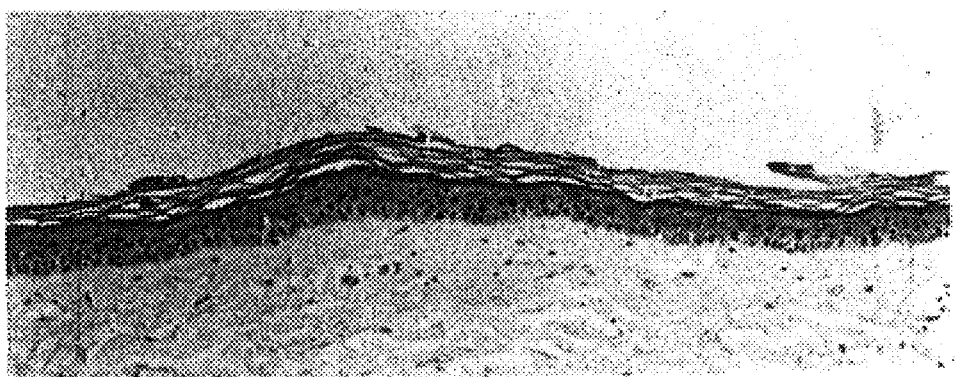
FIG. 36 shows human skin irradiated at 50 mJ, which is an energy sufficient to make the skin permeable (to lidocaine, for instance) and yet does not show any sign of stratum corneum ablation.
Figure 37:
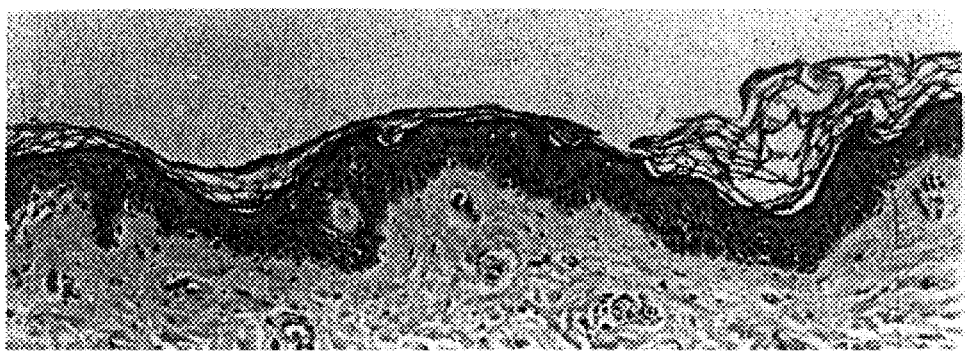
FIG. 37 shows human skin that was irradiated at 80 mJ. In this case, some change in the appearance of the sc has taken place (perhaps coagulation), and yet the sc is still intact.

Numerous in vivo experiments have been done on rats and humans. Usually, the skin is irradiated with the Er:YAG laser with a spot having a diameter of 2 mm and particular pulse energy, and then the irradiated site is biopsied immediately or 24 hours later. Two examples of typical results are shown in FIG. 36 and 37. FIG. 36 shows human skin irradiated at 50 mJ, which is an energy sufficient to increase the skin permeation (to lidocaine, for instance) and yet does not show any sign of stratum corneum ablation. FIG. 37 depicts human skin 24 hours after being irradiated at 80 mJ. In this case, some change in the appearance of the sc has taken place (perhaps coagulation of some layers of sc into a darkly staining single layer), and yet the sc is still mostly intact and is not ablated. Irradiation of human skin in vivo, and subsequently examined under a dissection microscope, shows that at subablative energies (less than about 90 to 120 mJ), the stratum corneum is still present on the skin. The sc appears slightly whitened, which might be evidence of desiccation.

Example 7

Figure 21:
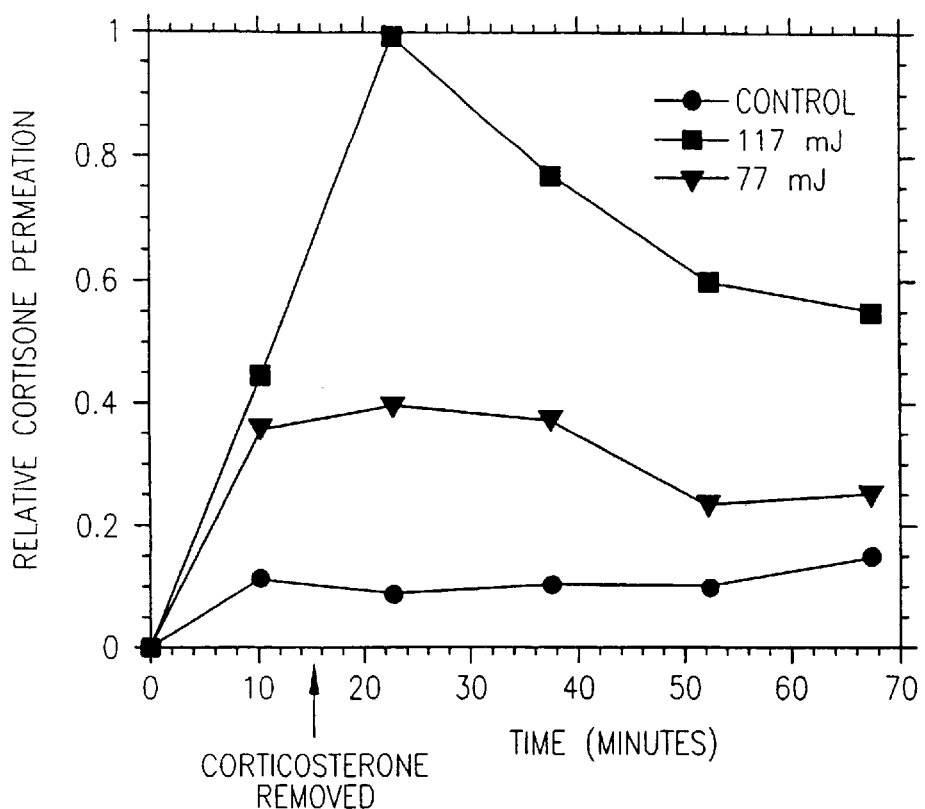
FIG. 21 is a chart showing a study using corticosterone which showed enhanced permeation (over controls) through skin irradiated at an energy of 77 mJ and 117 mJ.
Figure 22:
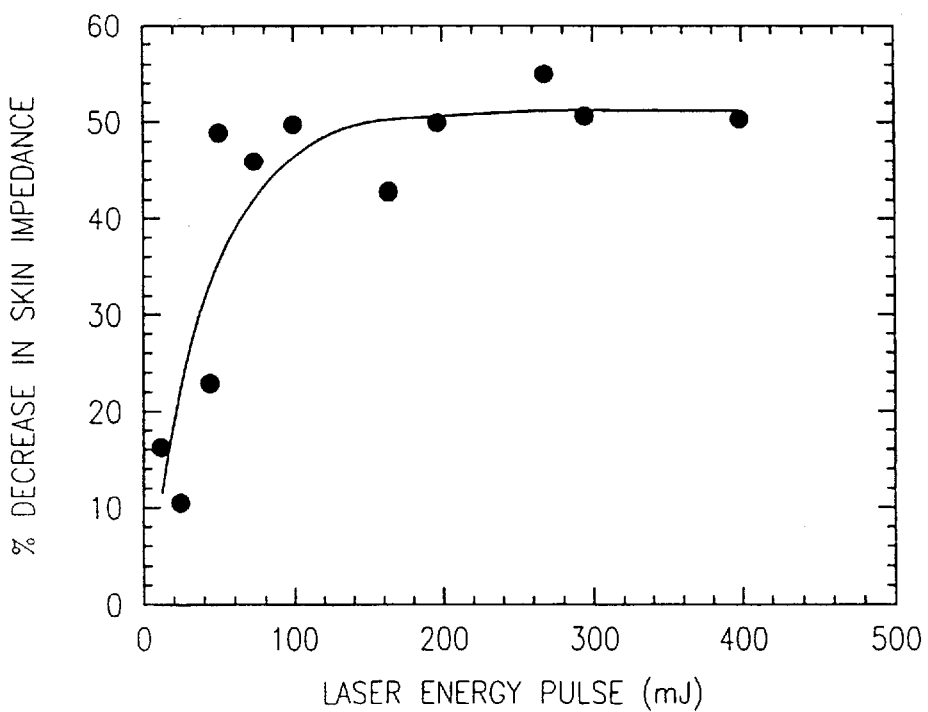
FIG. 22 shows that there is a decrease in skin electrical impedance through skin irradiated at energies as low as perhaps 10 mJ, using the fitted curve to interpolate data.
Figure 23:
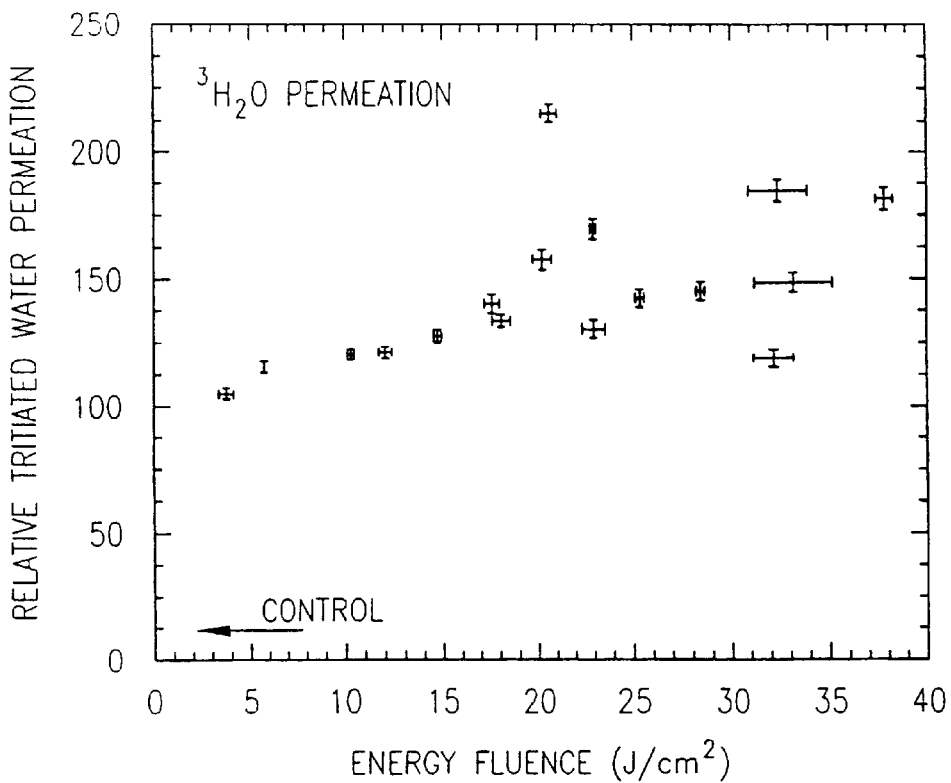
FIGS. 23–24 show, in a permeation study of tritiated water ($^3H_2O$ involving lased human skin at energies from 50 mJ (energy fluence, 1.6 J/cm$^2$) to 1250 mJ (40 J/cm$^2$), that an increase in permeation was seen in skin irradiated at low energies up to about 150 m.1 (5 J/cm$^2$), whereupon the permeation is more-or-less constant.
Figure 24:
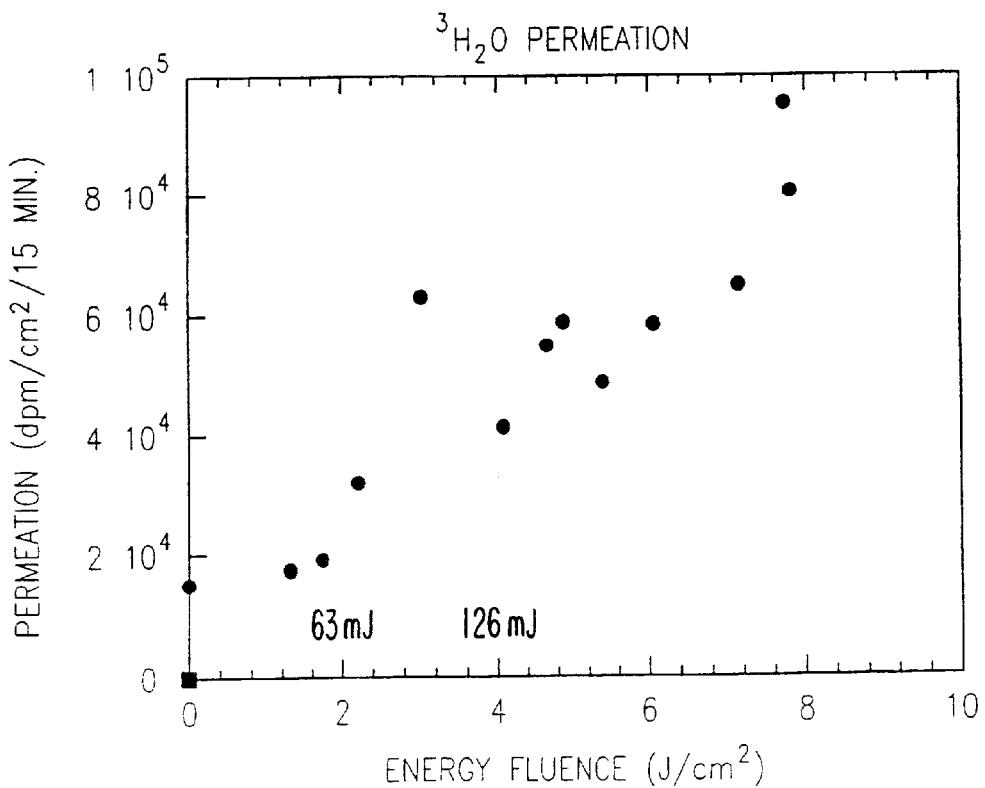
Figure 26:
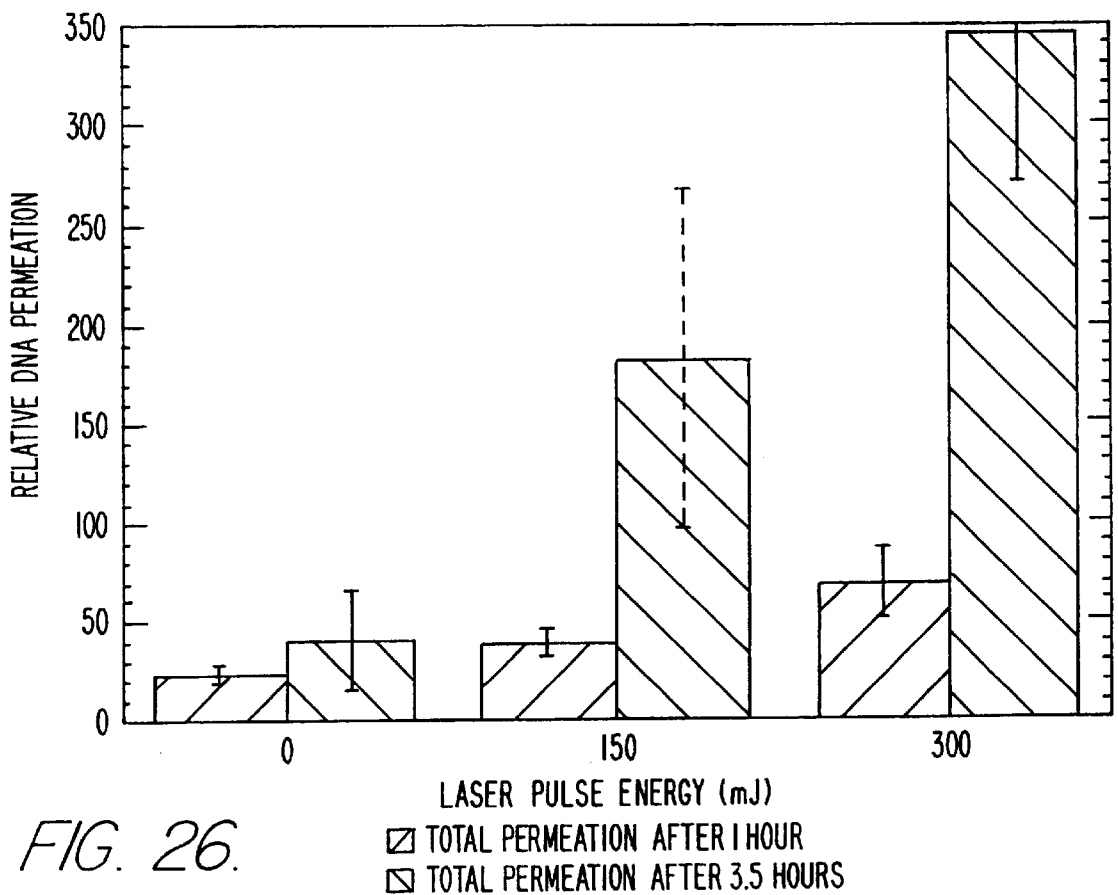
FIG. 26 is a chart of a study using DNA showing enhanced permeation (over controls) through skin irradiated at an energy of 150 mJ and 300 mJ.

FIG. 22 shows that there is a decrease in skin impedance in skin spots having a diameter of 2 mm, and irradiated at energies as low as 10 mJ, using the fitted curve to interpolate data. Histology studies on rat skin in vivo, however, showed no evidence of ablation at energies less than about 100 to 200 mJ. A similar histology study on human skin in vitro did not show any sign of ablation until about 140 mJ laser pulses were applied. Repeating this study showed the same result as the previous studies. A permeation study of tritiated water ($^3H_2O$) involving lased human skin at energies from about 50 mJ (1.6 j/cm$^2$) to 1250 mJ (40 J/cm$^2$) determined (see FIGS. 23 and 24) that an increase in permeation was seen at low energies up to about 150 mJ (5 J/cm$^2$) whereupon the permeation is more-or-less constant. Again, it appears that there has been an enhancement of permeation (of tritiated water) at energies that are sub-ablative. Two more examples are: corticosterone (FIG. 21) showed enhanced permeation (over controls) at an energy of about 77 mJ, whereas using DNA (FIG. 26) showed enhanced permeation at an energy of about 150 mJ. Although it is not clear whether the latter is or is not an ablative energy, other molecules similar to DNA (such as RNA) may also benefit from this subablative irradiation protocol.

Figure 25:
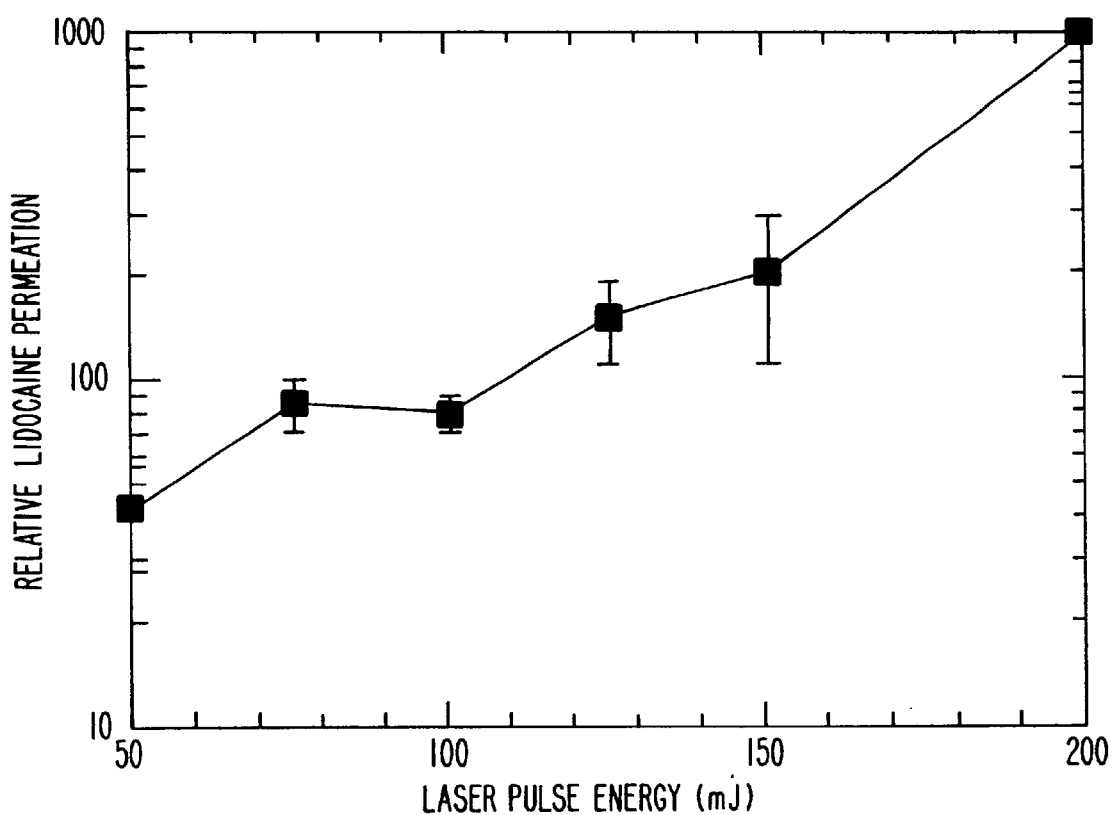
FIG. 25 is a chart showing permeation of lidocaine through skin in vitro.

As shown in FIG. 25, we determined that we could enhance the permeation of lidocaine through laser irradiated skin in vitro. Subsequently, we determined, empirically, that we could get anesthesia at sub-ablative energies (between about 50 and 100 mJ) using concentrated lidocaine applied on the laser irradiated skin for up to 6 minutes or so. To get weaker lidocaine to permeate to an efficacious concentration in short periods of time, energies in the range of about 150 to 250 mJ were required. However, it is believed that, for superficial anesthesia, energies below 50 mJ may be effective. If deeper anesthesia is directed, the weaker lidocaine must be administered for a greater length of time.

Example 8

The output of the Er:YAG laser was passed through an aperture to define its diameter as 2 mm. Human skin, purchased from a skin bank, was positioned in Franz diffusion cells. The receptor chamber of the cell was filled with 0.9% buffered saline. A single pulse of measured energy was used to irradiate the skin. Control skin was left unirradiated. When the permeation of lidocaine was to be tested, a 254 mJ pulse was used, and multiple samples were irradiated. In the case of y-interferon, a 285 mJ pulse was used, and multiple samples were irradiated. In the case of insulin, a 274 MJ pulse was used, and multiple samples were irradiated. In the case of corticosterone, either a 77 n-J or 117 mJ pulse was used. After irradiation, a stirring magnet was placed in the receptor chamber of the diffusion cells and the cells were placed in a heating block held at 37° C. The radiolabeled lidocaine, y-interferon insulin and corticosterone were diluted in buffered saline, and 100 µl of the resulting solutions was placed in the donor chamber of separate diffusion cells. The donor was left on the skin for the duration of the experiment (in the case of lidocaine, insulin and y-interferon, or 15 minutes in the case of corticosterone). At various times post-drug-application, samples were taken from the receptor chamber and the amount of drug present was assayed with either a gamma-counter, or a liquid scintillation counter. Graphs of the resulting data are shown in FIGS. 21, 3 9, 40 and 41. From this, and similar data, the permeability constants $k_p$ of three of the tested drugs were derived; they are:

| Drug | Permeability Constant, $k_p$ ($\times 10^{-3}$ cm/hr) |
| --- | --- |
| Lidocaine | 2.62 ± 6.9 |
| γ-Interferon | 9.74 ± 2.05 |
| Insulin | 11.3 ± 0.93 |

Example 9

Figure 38A:
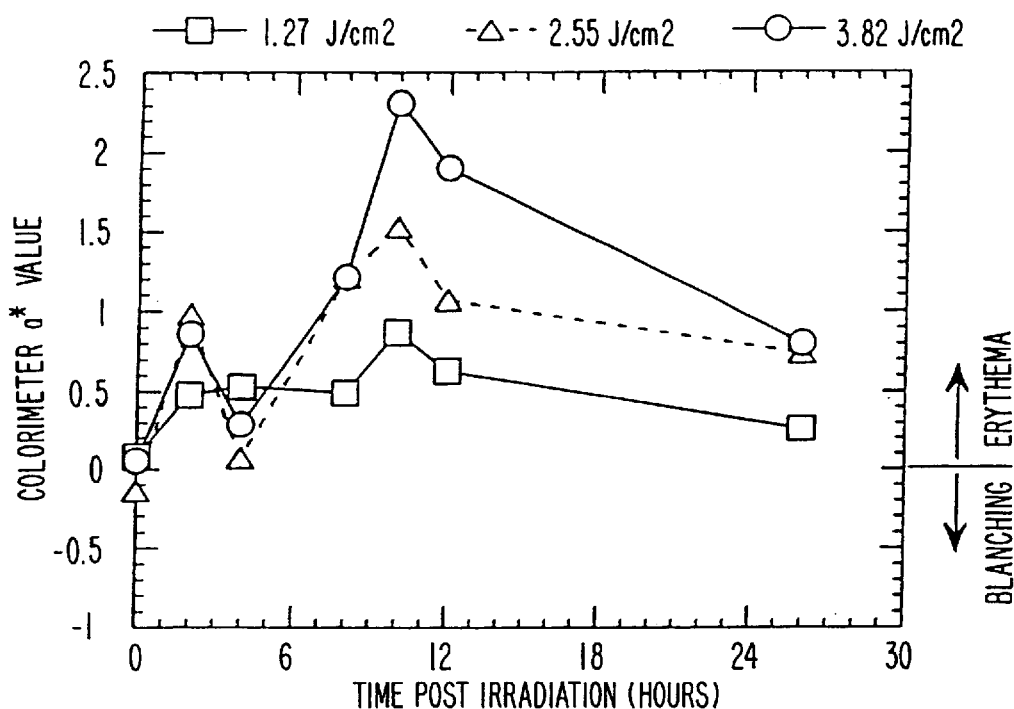
FIG. 38 shows in vivo blanching assay results.
Figure 38B:
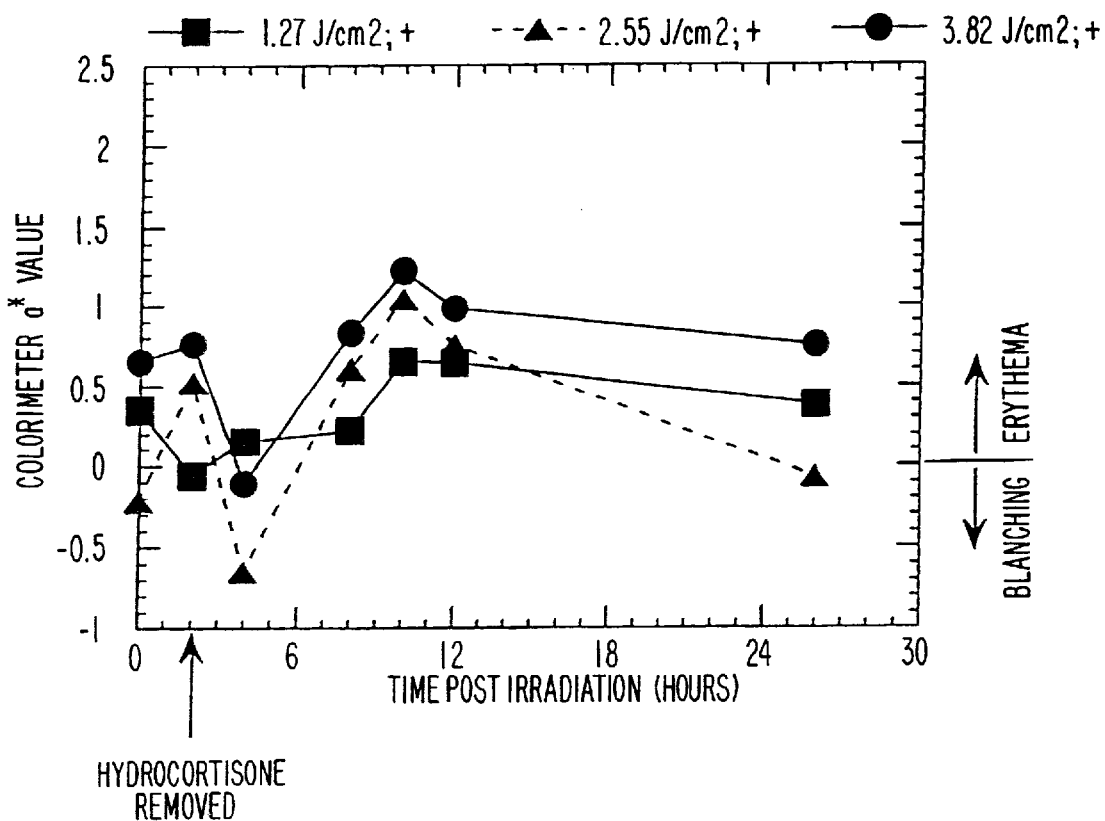
Figure 39:
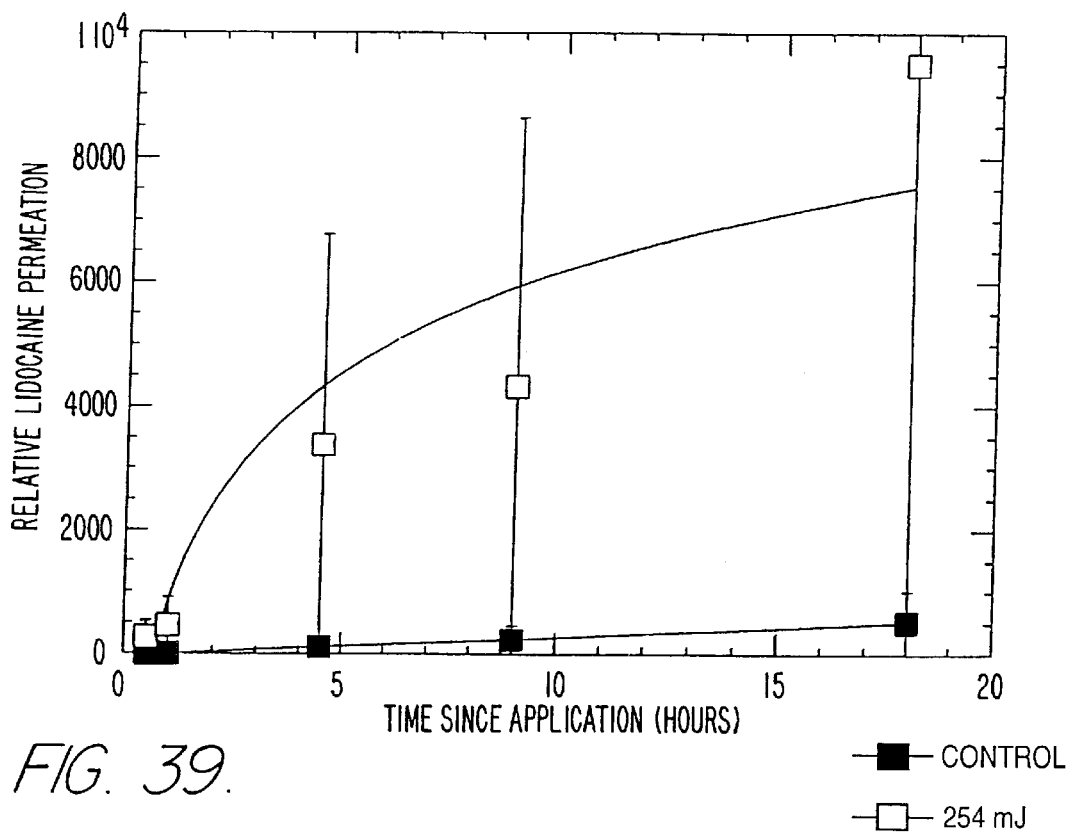
FIG. 39–41 shows permeation of lidocaine, insulin and y-interferon through human skin in vitro.
Figure 40:
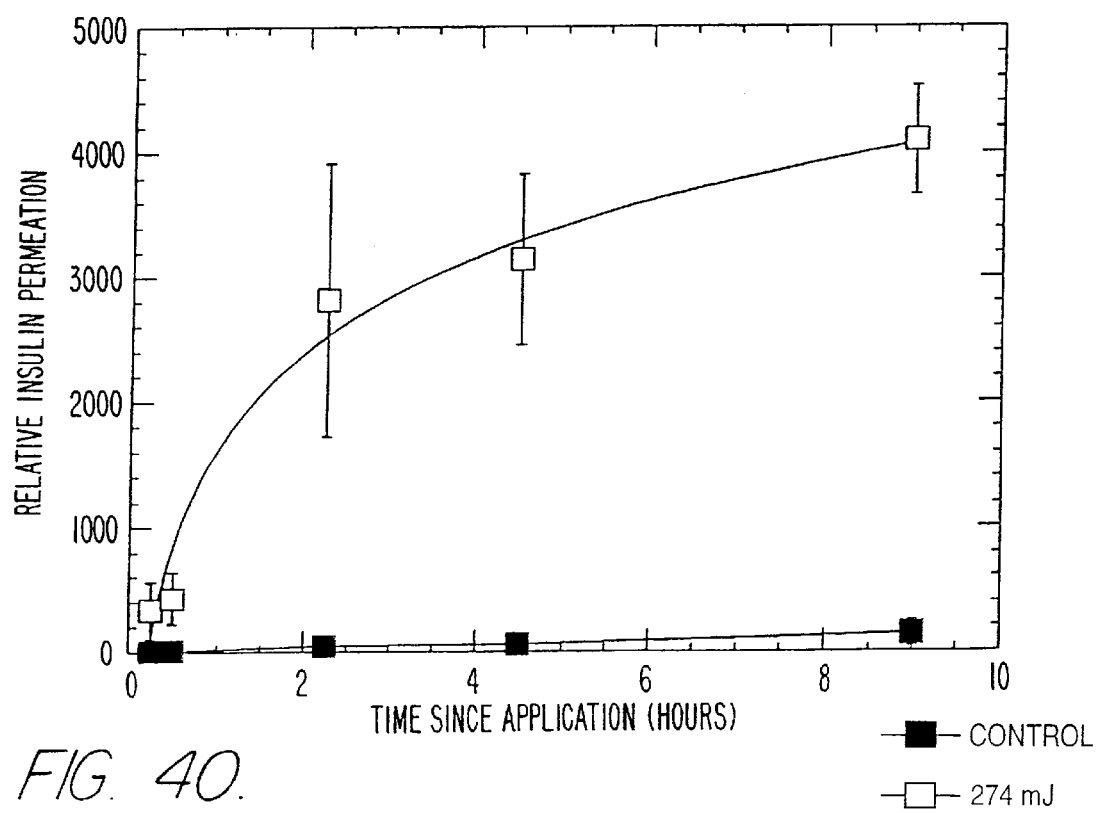
Figure 41:
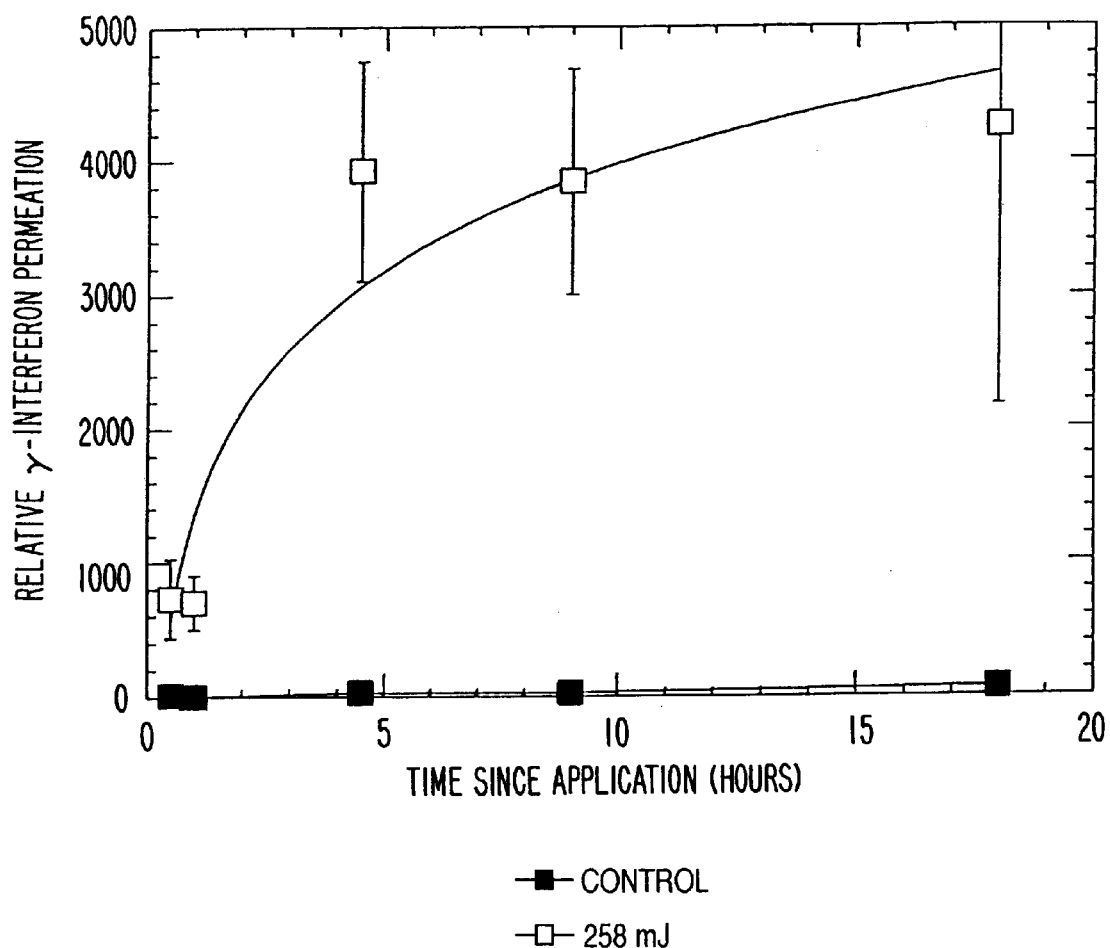

This data was collected during the same experiment as the TEWL results (see Example 1 and FIG. 27). In the case of the blanching assay, baseline skin color (redness) measurements were taken of each spot prior to irradiation, using a Minolta CR-300 Chronometer (Minolta Inc., N.J.). The Er:YAG laser was then used to irradiate six 2 mm spots on one forearm, at energies of about 40, 80 and 120 mJ. A spot (negative colorimeter control) directly adjacent to the laser irradiated spots remained untouched. Subsequently, a thin film of 1% hydrocortisone ointment was applied to three of the lased spots on the treatment arm. One untouched spot on the contralateral arm was administered a thin layer of Diprolene (beta-methasone), which is a strong steroid that can permeate the intact stratum corneum in an amount sufficient to cause measurable skin blanching. An occlusive patch, consisting of simple plastic wrap, was fixed with gauze and dermatological tape over all sites on both arms and left in place for two hours, after which the administered steroids were gently removed with cotton swabs. Colorimeter measurements were then taken over every unirradiated and irradiated spot at 2, 4, 8, 10, 12 and 26 hours post-irradiation; these results are shown in FIG. 38. Finally, the skin was clinically assessed for evidence of irritation at the 26 hour evaluation. The results of the chromameter measurements show that some erythema (reddening) of the skin occurred but, because of the opposite-acting blanching permeating hydrocortisone, the reddening was less than that seen in the control spots which did not receive hydrocortisone. The Diprolene control proved the validity of the measurements and no problems were seen in the volunteers at the 26 hour evaluation, although in some of the cases, the site of irradiation was apparent as a small red spot.

Example 10

The radiant output of the Er:YAG laser is focussed and collimated with optics to produce a spot size at the surface of the skin of, for example, 5 mm. The skin of the patient, being the site of, or close to the site of, disease is visually examined for anything that might affect the pharmacokinetics of the soon-to-be administered drug: e.g., significant erythema or a wide-spread loss of the integrity of the stratum corneum. This site, which will be the site of irradiation, is gently cleansed to remove all debris and any extraneous compounds such as perfume or a buildup of body oils. A disposable tip, attached to the laser pressed up to the skin prior to irradiation, is used to contain any ablated biological debris, as well as to contain any errant radiant energy produced by the laser. A single laser pulse (approximately 350 microseconds long), with an energy of about 950 mJ, is used to irradiate a spot of skin having a diameter of 5 mm. The result is a reduction or elimination of the barrier function of the stratum corneum. Subsequently, an amount of pharmaceutical, hydrocortisone for example, is spread over the irradiation site. The pharmaceutical may be in the form of an ointment so that it remains on the site of irradiation. Optionally, an occlusive patch is placed over the drug in order to keep it in place over the irradiation site.

Example 11

In vivo Skin Impedance Pilot Experiment
A. Laser Ablation:
The 2.94 micron radiant energy output of the Venisect Er:YAG laser was passed through an iris with a 2 mm. diameter. The energy output of the laser was measured with a calibrated Ophir energy/power meter (Opti-Optronics, Inc., Peabody, Mass.). A single ablation on the volar aspect of the forearm of a volunteer was done. Three ECG electrodes (Medi-Trace, Buffalo, N.Y.) were applied to the arm; one near the wrist as a reference site, one over the site of irradiation, and one adjacent to the site of irradiation.

Figure 42:
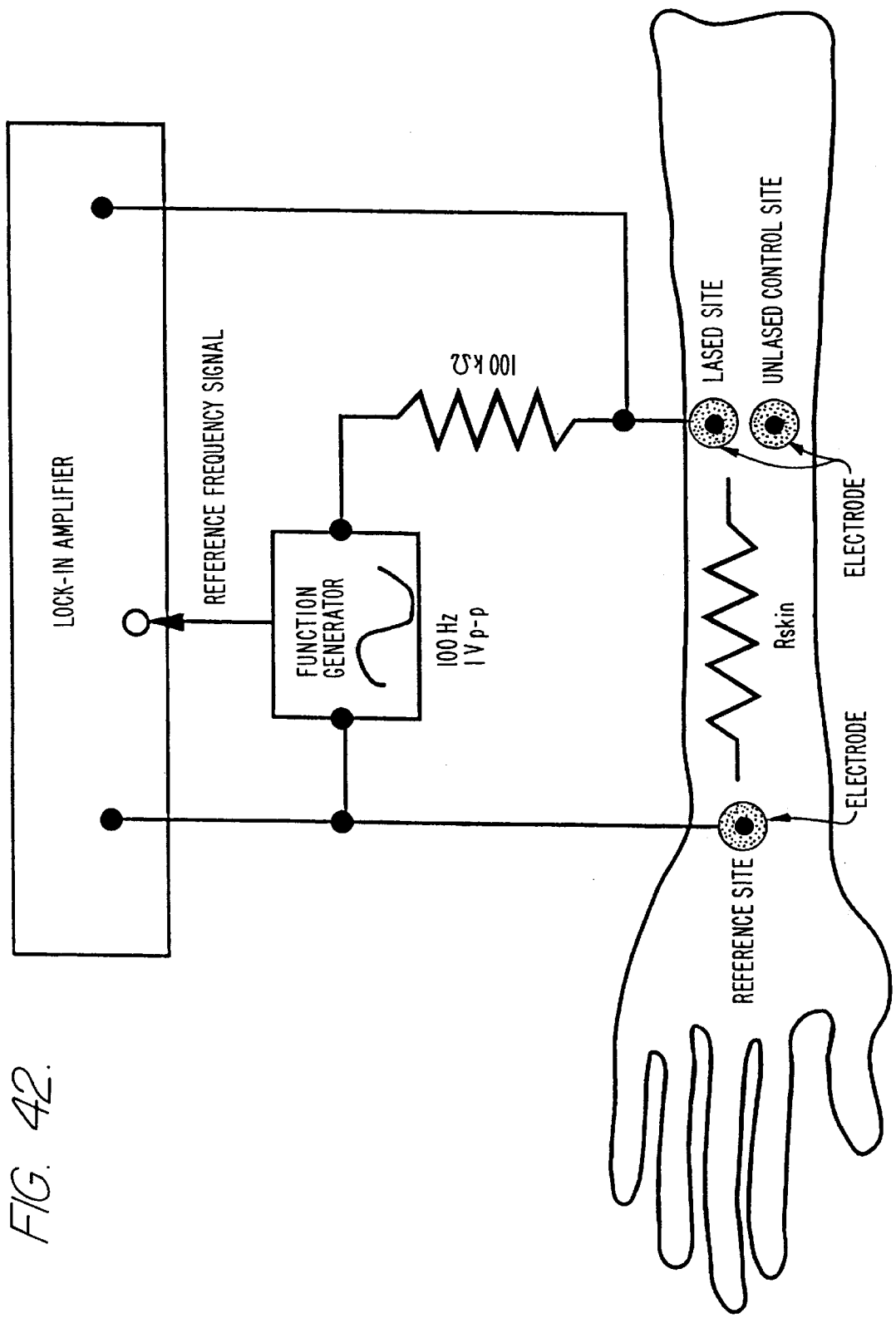
FIG. 42 shows the experimental arrangement to measure the electrical impedance of human skin in vivo.
Figure 43A:
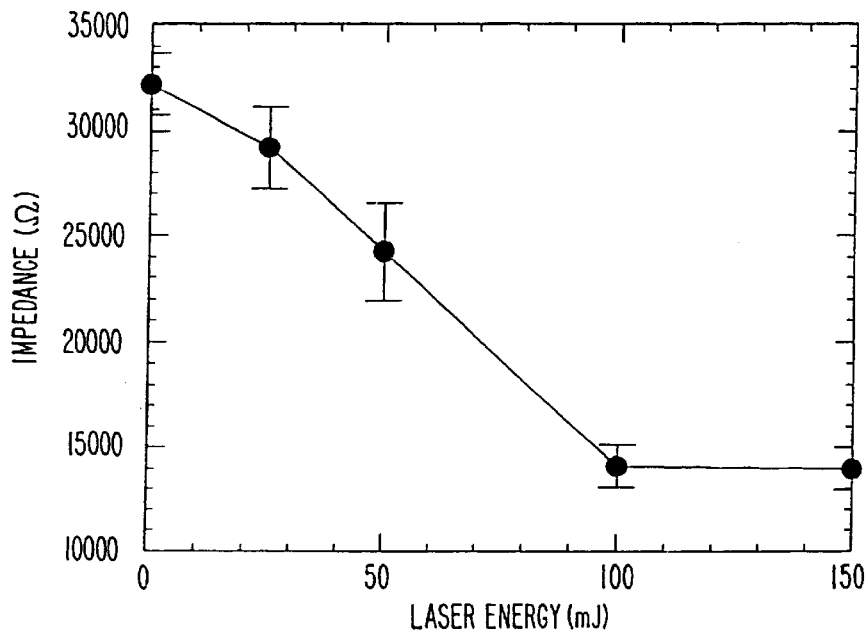
FIG. 43 shows in vivo human skin electrical impedance as a function of Er:YAG laser pulse energy; and in vivo human skin impedance as a function of days post laser irradiation and laser pulse energy.
Figure 43B:
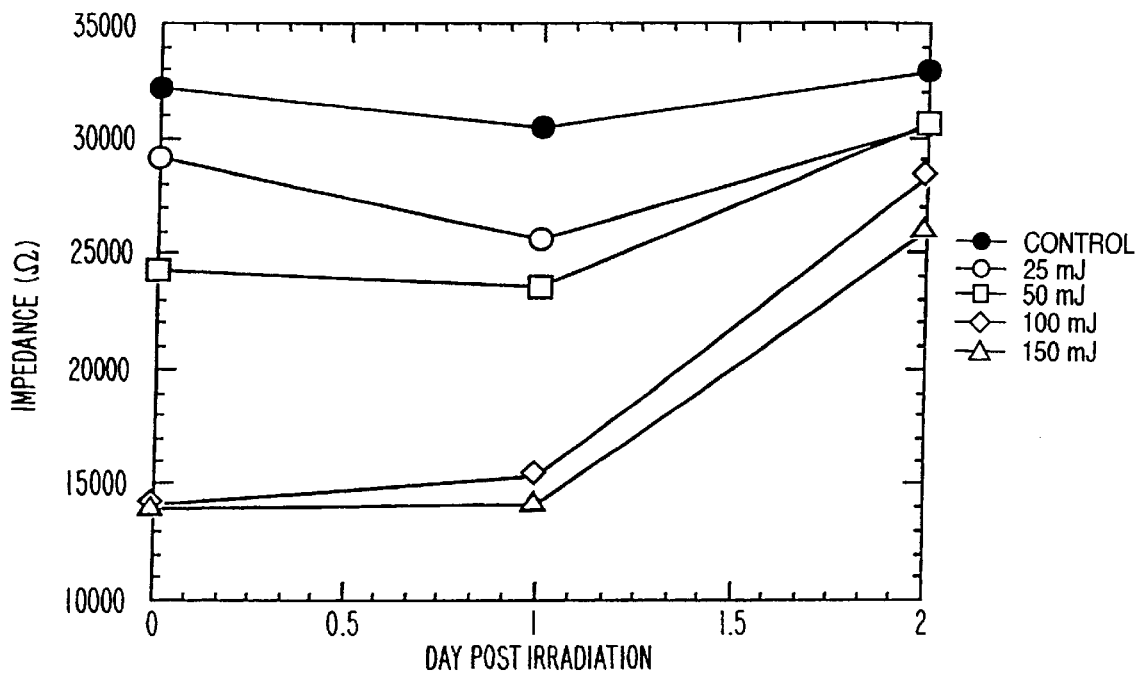

B. Electrical Measurements:
Electrical measurements were made using a lock-in amplifier (Stanford Research Systems, Sunnyvale, Calif.). One volt peak-to-peak was maintained at 100 Hz throughout the testing period using a constant voltage function generator (Stanford Research Systems, Calif.). Medi-Trace S'Offset ECG electrodes were used to deliver and measure the electrical energy and to test the impedance of the skin. Measurements were taken within about 10 minutes of laser irradiation. A diagram of the experimental arrangement is shown in FIG. 42.
C. Results:
The results of this experiment are shown in FIGS. 22 and 43. In the case of FIG. 22, the impedance of the lased site was compared to twice the impedance of the unlased site, and the change was expressed as a percentage drop in impedance. Note that the threshold for stratum corneum ablation varies from about 80–120 mJ (as measured by visualizing the ablation of stratum corneum placed on microscope slides). Subablative irradiations still result in a reduction in impedance.

Example 12

In vivo Skin Impedance Human Study

The arms of subjects were gently shaved with an electric razor to prevent hair follicles from interfering with the measurements and to ensure good contact from electrode to skin. The subjects were marked with a black felt marker in five diamond shaped areas on each arm. The testing period lasted for three days, taking measurements on each arm each day.
A. Laser Ablation:
Approximately 2 mm-diameter spots on the subjects' arms were ablated using radiant energy produced by the Venisect Er:YAG laser. The energy of each pulse was measured beforehand using an Ophir Nova model energy meter. Separate spots on each arm of each subject were exposed to laser pulses of 25, 50, 100, and 150 mJ respectively. Each of these lased areas was positioned in one of the four diamond shaped areas on an arm, with the fifth area being an unlased control. After irradiation, the impedance of the lased skin on the subjects' arms was measured.
B. Electrical Measurements and Results:
Electrical measurements were made using the arrangement shown in FIG. 42. Measurements were taken on three successive days to determine how the level of healing affected impedance (FIG. 43). As a consequence of irradiation, the impedance of tie skin is significantly reduced. Moreover, the loss in impedance recovers over a period of time.

Example 13

In vitro Skin Permeation

Skin samples were prepared the same as was done for the in vitro impedance study (Example 11). The skin sections were cut to a size of about 0.227 cm$^2$. These samples were then placed in Franz diffusion cells. The loaded Franz cells were filled with a nonsterile PBS solution on the subcutaneous surface of the skin. A micro-stirring bar was placed in the cell also. Each Franz cell was placed in a PMC Dataplate stirring digital dry block heater maintained at 37° C.
A. Exposure to Methanol and Chloroform;
The test samples were loaded with about 100 μl of a methanol/chloroform solution on the stratum corneum side of the samples, the solvent was left for a period of about 5 minutes. The solvent was then removed with a micropippetter and cotton swabs. About 100 µl of tritiated water was then placed on the stratum corneum side of the test sample and left to permeate for about 1 hour. After one hour had passed the tritiated water was removed using a micropippetter and cotton swabs. About 1 ml of the PBS from the subcutaneous side of the skin was removed with a syringe and added to about 5 ml of scintillation fluid in a scintillation vial. This was done with each sample and a control, which was made using PBS that was fresh from the bottle. Another control was made using the same procedure as above except that the skin had not had any chemical treatment before application of the tritiated water.

B. Exposure to Methanol, Chloroform and Glacial Acetic Acid

The test samples were loaded with about 100 µl of a methanol/chloroform/glacial acetic acid solution on the stratum corneum side of the samples. The solvent was left for a period of about 5 minutes, The solvent was then removed with a micropippetter and cotton swabs. About 100 µl of tritiated water was then placed on the stratum corneum side of the test sample and left to permeate for about 1 hour. After one hour had passed the tritiated water was removed using a micropippetter and cotton swabs. 1 ml of the PBS from the subcutaneous side of the skin was removed with a syringe and added to 5 ml of scintillation fluid in a scintillation vial. This was done with each sample and a control, which was made using PBS that was fresh from the bottle. Another control was made using the same procedure as above except that the skin had not had any chemical treatment before application of the tritiated water.

C. Exposure to Beta-Mercaptoethanol

The test samples were loaded with about 100 µl of β-mercaptoethanol on the stratum corneum side of the samples. The solvent was left for a period of about 5 minutes. The solvent was then removed with a micropippetter and cotton swabs. About 100 µl of tritiated water was then placed on the stratum corneum side of the test sample and left to permeate for about 1 hour. After one hour had passed the tritiated water was removed using a micropippetter and cotton swabs. 1 ml of the PBS from the subcutaneous side of the skin was removed with a syringe and added to 5 ml of scintillation fluid in a scintillation vial. This was done with each sample and a control, which was made using PBS that was fresh from the bottle. Another control was made using the same procedure as above except that the skin had not had any chemical treatment before application of the tritiated water.

D. Exposure to Steam (Thermal Denaturation)

The test samples were suspended above a beaker of boiling water (100° C. and the stratum corneum side of the samples was exposed to the steam. The samples were left for a period of about 3 minutes. About 100 µl of tritiated water was then placed on the stratum corneum side of the test sample and left to permeate for about 1 hour. After one hour had passed, the tritiated water was removed using a micropippetter and cotton swabs. About 1 ml of the PBS from the subcutaneous side of the skin was removed with a syringe and added to about 5 ml of scintillation fluid in a scintillation vial. This was done with each sample and a control, which was made using PBS that was fresh from the bottle. Another control was made using the same procedure as above except that the skin had not had any chemical treatment before application of the tritiated water.

E. Electrical Measurements and Results.

Figure 44:
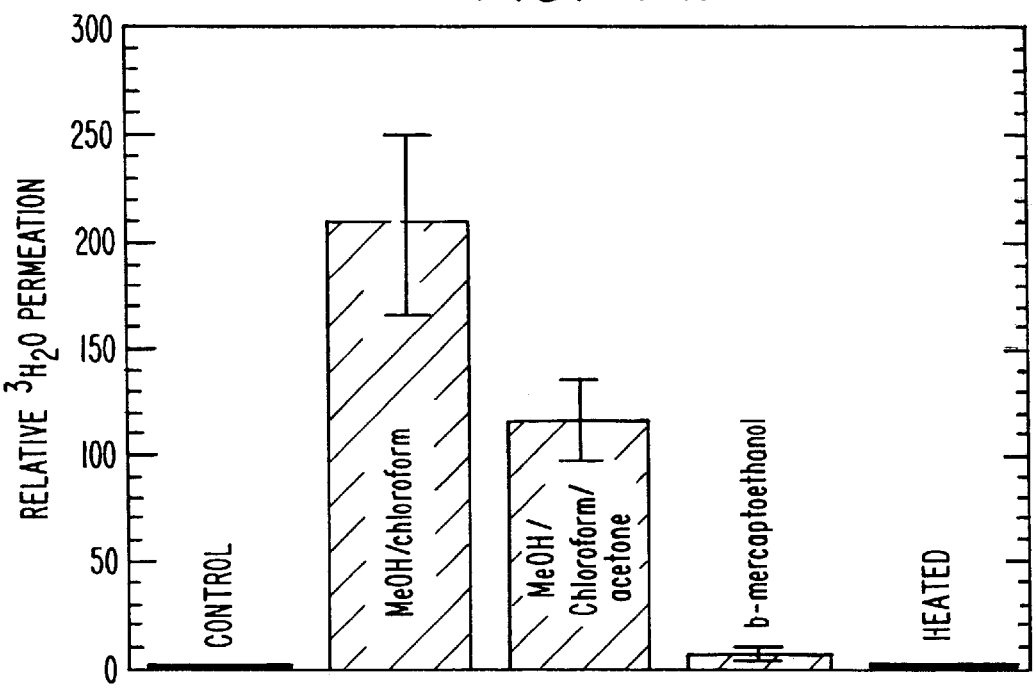
FIG. 44 shows in vitro human skin permeation of tritiated water as a function of prior treatment with a solvent or denaturant.

The results of this experiment appear in FIG. 44.

Example 14

Lidocaine Ionotophoresis

Skin samples were prepared the same as was done for the in vitro permeation study (Example 8). These samples were then placed in Franz diffusion cells. The samples of skin were irradiated using the same protocol as described in Example 8, lasing approximately 2 mm spots of skin using single pulses of about 175 mJ. Afterwards, 275 µl of 4% lidocaine without epinephrine, spiked with $^{14}$C-lidocaine, was placed in the donor cells. Electrodes, consisting of silver needles (nerve conduction electrodes) were placed in the donor and receptor chamber of the Franz cells. The voltage and current (supplied by a regulated d.c. power supply) applied to the electrodes were monitored by two digital multimeters. The voltage (0, 50, 125, or 250 mV) was applied for about 15 minutes (FIG. 45) or for about five hours (FIG. 46) at the set voltage of 50 mV.

Figure 45:
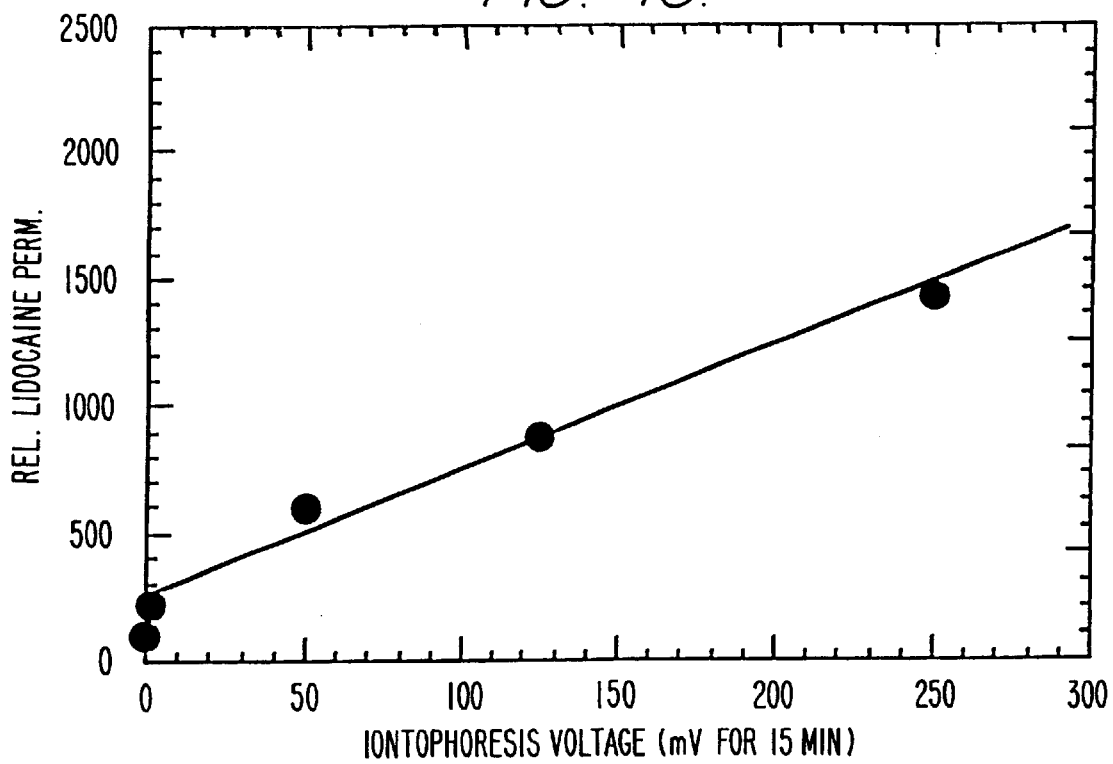
FIG. 45 shows enchanced lidocaine permeation through skin in vitro as a function of iontophoretic voltage.

The results of the 15-minute current, appearing on FIG. 45, indicate that permeation of lidocaine through irradiated skin increases with increasing applied voltage.

Figure 46:
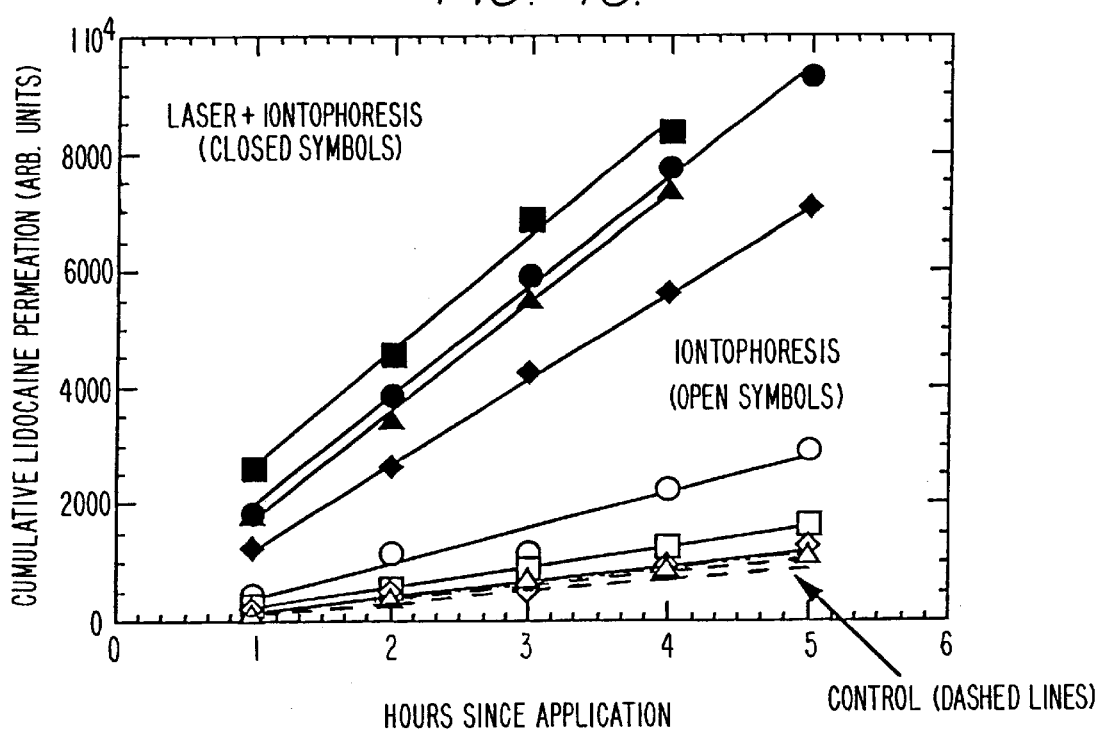
FIG. 46 shows cumulative lidocaine permeation through human skin in vitro as a function of time.

The results of the 5-hour current, appearing in FIG. 46, indicate that permeation of lidocaine through irradiated skin, and enhanced by iontophoresis, is greater than permeation through unirradiated skin or skin irradiated but not subjected to iontophoresis. The applied electrical current did not change during the experiment, indicating that polarization of the skin did not take place. The cumulative lidocaine permeation was linear with time, indicating that there was no electrically induced damage to the skin.

While applications of this invention have been shown and described, it would be apparent to those skilled in the art that many more modifications are possible without departing from the inventive concepts herein. The invention, therefore, is not to be restricted except in the spirit of the appended claims.

We claim:

1. A method of introducing a substance into a living body, comprising:
    forming an area on the stratum corneum of the skin of a living body having enhanced permeability through to the capillary layer by irradiating the skin with subablative laser energy without substantially ablating the skin; and
    introducing the substance into the body by bringing the substance in contact with the area of enhanced permeability.

2. The method of claim 1, wherein forming the area comprises:
    irradiating the skin with laser energy selected from the group consisting of Er:YAG, pulsed $CO_2$, Ho:YAG, Er:YAP, Er/Cr:YSGG, Ho;YSGG, Er:GGSG, Er:YLF, Tm:YAG, Ho/Nd:YA $10_3$, cobalt:$MgF_2$, HF chemical, DF chemical, carbon monoxide, deep LJV laser, diode laser, frequency tripled Nd:YAG, and combinations thereof.

3. The method of claim 2, wherein irradiating the skin comprises:
    irradiating the skin with subablative laser energy having a wavelength of about 1.5 to about 10 microns, an energy fluence of about 0.1 to about 100,000 J/cm$^2$, and a target area on the skin of about 0.001 to about 10 mm in diameter.

4. The method of claim 3, wherein irradiating the skin comprises;
    irradiating the skin with subablative laser energy having a wavelength of approximately 2.94 microns.

5. The method of claim 1, wherein forming the area comprises:
    irradiating the skin with laser energy selected from the group consisting of gated, continuous wave, modulated diode, or pulsed laser radiant energy.

6. The method of claim 5, wherein irradiating the skin comprises:
   irradiating the skin with subablative laser energy having a wavelength of about 1.5 to about 10 microns, an energy fluence of about 0.1 to about 100,000 J/cm$^2$, and a target area on the skin of about 0.001 to about 10 mm in diameter.

7. The method of claim 6, wherein irradiating the skin comprises;
   irradiating the skin with subablative laser energy having a wavelength of approximately 2.94 microns.

8. The method of claim 1, wherein the substance is selected from the group of in vivo diagnostic substances consisting of contrasting imaging agents, radionuclide based agents, and combinations thereof.

9. The method of claim 1, wherein the substance is selected from the group of systemically active substances consisting of neuroactive agents, auto acids, anti-hypertensives, anti-arrhythmics, hormones, chemotherapy antiparasitic agents, chemotherapy anti-microbial agents, and combinations thereof.

10. The method of claim 1, wherein the substance is selected from the group of locally active substances consisting of lidocaine, anesthetic agents, erectile dysfunction agents, metabolic inhibitors, steroidal or nonsteroidal anti-inflammatory agents, vitamins, retinoids, anticancer agents, antibodies, antibody conjugates, and combinations thereof.

11. The method of claim 1, wherein the substance is selected from the group consisting of protein based pharmaceutical substances, DNA based pharmaceutical substances, RNA based pharmaceutical substances, and combinations thereof.

12. The method of claim 11, wherein the protein based substance is selected from the group consisting of cytokines, hormones, cell activation factors, cellular inhibitors, proteases, protease inhibitors, clotting factors, and combinations thereof.

13. The method of claim 11, wherein the DNA or RNA based substance is selected from the group consisting of oligonucleotides, gene therapy agents, ribozymes, and combinations thereof.

14. The method of claim 1, wherein the substance is selected from the group of antimicrobial chemotherapy agents consisting of anti-infectives, antifungals, antivirals, and combinations thereof.

15. The method of claim 1, wherein the substance is selected from the group of immunity generating substances consisting of vaccines, antigens, immunogen preparations, and combinations thereof.

16. The method of claim 1, wherein the substance is selected from the group of permeation enhancing substances consisting of dimethyl-sulfoxide, alcohol, Azone, pentaerythritrol dioleat, lauramide DEA, polyethyleneglycol-10 laurate, nonoxynol-10, propylene glycol, urea, water, n-propanol, amines, amides, pyrrolidones, surfactants, fatty acids, liposomes, and combinations thereof.

17. The method of claim 1, wherein bringing the substance in contact with the area of enhanced permeability comprises:
   bringing the substance in direct contact with interstitial fluid from within the body.

* * * * *

UNITED STATES PATENT AND TRADEMARK OFFICE
CERTIFICATE OF CORRECTION

PATENT NO. : 6,419,642 B1 Page 1 of 1
DATED : July 16, 2002
INVENTOR(S) : Kevin S. Marchitto et al.

It is certified that error appears in the above-identified patent and that said Letters Patent is hereby corrected as shown below:

Column 6,
Line 8, "m.1" should be -- mJ --.
Lines 26 and 27, "(ºC." should be -- (ºC --.
Line 27, "of-the" should be -- of the --.
Line 56, "y-interferon" should be -- $\gamma$-interferon --.

Column 11,
Line 66, "E1" should be -- E1 --.

Column 24,
Lines 54 and 55, "(ºC." should be -- (ºC --.

Column 6,
Lines 40 and 45, "y-interferon" should be -- $\gamma$-interferon --.
Line 50, "3 9" should be -- 39 --.

Signed and Sealed this

Eighth Day of July, 2003

JAMES E. ROGAN
*Director of the United States Patent and Trademark Office*